United States Patent [19]
Joseph et al.

[11] Patent Number: 5,837,535
[45] Date of Patent: Nov. 17, 1998

[54] NEURONAL-NEONATAL GENE: NEURONATIN

[75] Inventors: Rajiv Joseph, Birmingham; Dexian Dou, Dearborn, both of Mich.

[73] Assignee: Henry Ford Health System, Detroit, Mich.

[21] Appl. No.: 602,093

[22] Filed: Feb. 15, 1996

Related U.S. Application Data

[63] Continuation-in-part of Ser. No. 259,299, Jun. 13, 1994, abandoned.

[51] Int. Cl.[6] .......................... C12N 15/85; C12N 15/63; C12N 15/11
[52] U.S. Cl. .......................... 435/325; 435/357; 435/368; 435/320.1; 435/252.3; 536/23.1; 536/24.1
[58] Field of Search ................................ 536/23.1, 23.5, 536/24.1; 435/320.1, 252.3, 325, 357, 368

[56] References Cited

U.S. PATENT DOCUMENTS

| | | | |
|---|---|---|---|
| 3,791,932 | 2/1974 | Schuurs et al. | 195/103.5 R |
| 3,839,153 | 10/1974 | Schuurs et al. | 195/103.5 R |
| 3,850,578 | 11/1974 | McConnell | 23/230 B |
| 3,850,752 | 11/1974 | Schuurs et al. | 195/103.5 R |
| 3,853,987 | 12/1974 | Dreyer | 424/1 |
| 3,867,517 | 2/1975 | Ling | 424/1 |
| 3,879,262 | 4/1975 | Schuurs et al. | 195/99 |
| 3,901,654 | 8/1975 | Gross | 23/230 B |
| 3,935,074 | 1/1976 | Rubenstein et al. | 195/103.5 R |
| 3,984,533 | 10/1976 | Uzgiris | 424/23 |
| 3,996,345 | 12/1976 | Ullman et al. | 424/23 |
| 4,034,074 | 7/1977 | Miles | 424/23 |
| 4,098,876 | 7/1978 | Piasio et al. | 424/23 |
| 4,666,828 | 5/1987 | Gusella | 435/6 |
| 4,683,202 | 7/1987 | Mullis | 435/91 |
| 4,736,866 | 4/1988 | Leder et al. | 800/435 |
| 4,801,531 | 1/1989 | Frossard | 435/6 |
| 4,879,219 | 11/1989 | Wands et al. | 435/530 |
| 5,011,771 | 4/1991 | Bellet et al. | 435/7.94 |
| 5,175,383 | 12/1992 | Leder et al. | 800/2 |
| 5,175,384 | 12/1992 | Krimpenfort et al. | 800/2 |
| 5,175,385 | 12/1992 | Wagner et al. | 800/2 |
| 5,192,659 | 3/1993 | Simons | 435/6 |
| 5,221,778 | 6/1993 | Byrne et al. | 800/2 |
| 5,272,057 | 12/1993 | Smulson et al. | 435/6 |
| 5,281,521 | 1/1994 | Trojanowski et al. | 435/7.5 |
| 5,288,846 | 2/1994 | Quertermous et al. | 435/172.3 |
| 5,298,422 | 3/1994 | Schwartz et al. | 435/320.1 |
| 5,347,075 | 9/1994 | Sorge | 800/2 |
| 5,360,735 | 11/1994 | Weinshank et al. | 435/240.2 |
| 5,387,742 | 2/1995 | Cordell | 800/2 |

FOREIGN PATENT DOCUMENTS

| | | | |
|---|---|---|---|
| WO 9314200 | 5/1993 | WIPO | C12N 15/00 |
| WO 9406908 | 2/1994 | WIPO | C12N 15/00 |
| WO 9423049 | 8/1994 | WIPO | C12N 15/00 |
| WO 9428123 | 11/1994 | WIPO | C12N 15/00 |

OTHER PUBLICATIONS

Lomri et al. Gene 80(1989) 87–98.

Adams et al. Nature Genetics 4(1993) 373–380.

Adams and Rose, "Structural requirements of a membrane–spanning domain for protein anchoring and cell surface transport" *Cell*, 41:1007–1015 (1985).

Adunyah et al., "Structural and functional comparison of a 22 kDa protein from internal human platelet membranes . . . " *Biochim Biophys. Acta*, 941:63–70 (1988).

Barnes et al., "Kilo–sequencing: creation of an ordered nest of asymmetric deletions across a large target sequence . . . " *Meth Enzymol.*, 101:98–122 (1983).

Brandt et al., "Ring chromosome 20 with loss of telomeric sequences detected by multicolor PRINS" *Clin Genet*, 44:26–31 (1993).

Brown–Schimer et al., "Molecular cloning and chromosome mapping of the human gene encoding protein phosphotyrosyl phosphatase 1B" *Proc Natl Acad Sci USA*, 87:5148–5152 (1990).

Cherif et al., "Detection of single copy genes by nonisotopic in situ hybridization of human chormosomes" *Hum Genet*, 81:358–362 (1989).

Christy and Nathans, "DNA binding site of the growth factor–inducible protein zif268" *Proc Natl Acad Sci USA*, 86:8737–8741 (1989).

Cotter et al., "Deletion of the long arm of chromosome 20 in a patient with small cell lymphocytic lymphoma" *Cancer Genet Cytogenet*, 70:142–143 (1993).

Davis et al., "Hematologic manifestations associated with deletions of the long arm of chormosome 20" *Cancer Genet Cytogenet*, 12:63–71 (1984).

Diez–Martin et al., "Chromosome studies in 104 patients with polycythemia vera" *Mayo Clin Proc* 66:287–299 (1991).

Ey et al., "Giardia intestinalis: detection of major genotypes by restriction analysis of gene amplification products" *Int J Parasitol*, 23:591–600 (1993).

Faust et al., "Two related proteolipids and dolichol–linked oligosaccharides accumulate in motor neuron degeneration mice . . " *J Biol Chem*, 269:10150–10155 (1994).

(List continued on next page.)

*Primary Examiner*—Paula K. Hutzell
*Assistant Examiner*—Robert C. Hayes
*Attorney, Agent, or Firm*—Kohn & Associates

[57] ABSTRACT

The present invention is an isolated and purified DNA sequence which encodes a vertebrate mRNA for a neuron specific protein, neuronatin. The mRNA is selectively expressed in brain tissue during rapid brain growth when there is a surge in neuronal proliferation and migration and is repressed in adult tissue. In the human, the genomic DNA is as set forth in SEQ ID No:6 and the cDNA has a nucleotide sequence as set forth in SEQ ID No:5, with the gene mapped to human chromosome 20q11.2–12. The deduced protein is a proteolipid that appears to have a role in ion channel regulation during brain development.

10 Claims, 9 Drawing Sheets

OTHER PUBLICATIONS

Fearnley et al., "The sequence of the major protein stored in ovine ceroid lipofuscinosis is identical . . . " *Biochem J,* 268:751–758 (1990).

Hendricks–Taylor et al., "The CCAAT enhancer binding protein (c/EPBα) gene (CEBPA2) maps to human chromosome . . . " *Genomics,* 14:12–17 (1992).

Henikoff, "Unidirectional digestion with exonuclease III creates targeted breakpoints for DNA sequencing" *Gene,* 28:351–359 (1984).

Joseph et al., "Neuronatin mRNA: alternatively spliced forms of a novel brain–specific mammaliam developmental gene" *Brain Res.,* 690:92–98 (1995).

Kraner et al., "Silencing the type II sodium channel gene: a model for neural–specific gene regulation" *Neuron,* 9:37–44 (1992).

Krunze et al., "Localization of the active type I DNA topoisomerase gene in human chromosome 20q11.2–13.1 and two pseudogenes . . . " *Hum Genet,* 84:6–10 (1989).

Li et al., "Identification of a functional silencer element involved in neuron–specific expression of the synapsin–I gene" *Proc Natl Acad Sci USA,* 90:1460–1464 (1993).

Mandel et al., "cDNA sequence encoding the 16–kDa proteolipid of chromaffin granules implies gene duplication . . . " *Proc Natl Acad Sci USA,* 85:5521–5524 (1988).

Mercer et al., "Molecular cloning and immunological characterization of the γ–polypeptide . . . " *J Cell Biol,* 121:579–586 (1993).

Mierendoft and Pfeffer, "Direct sequencing of denatured plasmid DNA" *Meth Enzymol.,* 152:556–562 (1987).

Mohandas et al., "Regional localization of the human genes for S–adenosyl–homocysteine hydrolase . . . " *Hum Genet,* 66:292–295 (1984).

Moorman et al., "Unitary anion currents through phospholeman channel molecules" *Nature,* 377:737–740 (1995).

Moorman et al., "Phospholeman expression induces a hyperpolarization–activated choloride current in Xenopus oocytes" *J Biol Chem,* 267:14551–14554 (1992).

Mori et al., "A cell type–specific silencer element that controls the neural–specific expression of the SCG10 gene" *Neuron,* 4:583–594 (1990).

Morris et al., "Localization of the SRC oncogene to chromosome band 20q11.2 and loss of this gene . . . " *Blood,* 74:1768–1773 (1989).

Navarre et al., "Two distinct genes encode small isoproteolipids affecting plasma membrane . . . " *J Biol Chem,* 269:21262–21268 (1994).

Navarre et al., "A proteolipid associated with the plasma membrane H+–ATPase of fungi" *Ann NY Acad Sci,* 671:189–194 (1992).

Navarre et al., "Purification and complete sequence of a small proteolipid associated with the plasma membrane . . . " *J Biol Chem,* 267:6425–6428 (1992).

Nieto et al., "A receptor protein kinase implicated in the segmental patterning of the hindbrain and mesoderm" *Development,* 116:1137–50 (1992).

Palmer et al., "Purification and complete sequence determination of the major plasma membrane substrate for cAMP . . . " *J Biol Chem,* 266:11126–11130 (1991).

Palmer et al., "Mitochondrial ATP synthase subunit c storage in the ceroid–lipofuscinoses (Battent Disease)" *Am J Med Genet,* 42:561–567 (1992).

Pinkel et al., "Cytogenetic analysis using quantitative, high sensitivity, fluorescence hybridization" *Proc Natl Acad Sci USA,* 83:2934–2938 (1986).

Quintrell et al., "Identification of a human gene (HCK) that encodes a protein–tyrosine kinase and is expressed in hemopoietic cell" *Mol Cell Biol,* 7:2267–2275 (1987).

Simmerman et al., "Sequence analysis of phospholamban, identification of phosphorylation sites and two major structural domains" *J Biol Chem,* 261:13333–13341 (1986).

Suzuki and Wang, "Stimulation of bovine cardiac sarcoplasmic reticulum $Ca^2$ pump and blocking . . . " *J Biol Chem,* 261:7018–7023 (1986).

Tada, "Molecular structure and functional of phospholamban in regulating the calcium pump from sarcoplasmic reticulum" *Ann NY Acad Sci,* 671:92–103 (1991).

Tanford, "The hydrophobic effect and the organization of living matter" *Science,* 200:1012–1018 (1978).

Thiel et al., "Regulation of synapsin I gene expression by the zinc finger transcription factor . . . " *J Biol Chem,* 269:15294–15301 (1994).

Wawrzynow et al., "Sarcolipin, the proteolipid of skeletal muscle sarcoplasmic reticulum . . . " *Arch Biochem Biophys,* 298:620–623 (1992).

White et al., "Delection of chromosome 20q in myelodysplasia can occur in a multipotent precusor of both myeloid cells and B cells" *Blood,* 83:2809–2816 (1994).

Wijnholds et al., "Segment–specific expression of the neuronatin gene during early hindbrain development" *Dev Biol,* 171:73–84 (1995).

Wilkinson et al., "Segment–specific expression of a zinc–finger gene in the developing nervous system of the mouse" *Nature,* 337:461–464 (1989).

Zasloff, et al., "A new method for the purification and identification of covalently closed circular DNA molecules" *Nuc Acids Res,* 5:1139–1152 (1978).

Albert et al., "Distinct promoters directs neuronal and non-neuronal expression of rat aromatic L–amino acid decarboxylase" *Proc Natl Acad Sci USA,* 89:12053–12057 (1992).

Akiyama et al., "Gene structure and cell type–specific expression of the human ATP synthase α subunit" *Biochim. Biophys Acta,* 1219:129–140 (1994).

Balvay et al., "Pre–mRNA secondary structure and the regulation of splicing" *Bioessays,* 15:165–169 (1993).

Birnstiel et al., "Transcription termination and 3'processing: the end is in site?" *Cell,* 41:349–359 (1985).

Breathnach and Chambon, "Organization and expression of eukaryotic split genes coding for proteins" *Annu Rev Biochem,* 50:349–383 (1981).

Brunak et al., "Prediction of human mRNA donor and acceptor sites from the DNA sequence" *J Mol Biol,* 220:49–65 (1991).

Hawkins, "A survey on intron and exon lengths" *Nuc Acids Res,* 16:9893–9908 (1988).

Hirsch et al., "Identification of positive and negative regulatory elements governing cell–type–specific expression . . . " *Mol Cell Biol,* 10:1959–1968 (1990).

Ikemura, "Codon usage and tRNA content in unicellular and multicellular organisms" *Mol Biol Evol,* 2:13–34 (1985).

Jacobs et al., "Identification of a second promoter in the human c–myb proto–oncogene" *Oncogene,* 9:227–235 (1994).

Kudrycki et al., "Olf–1–binding sites: characterization of an olfactory neuron–specific promoter motif" *Mol. Cell Biol.,* 13:3002–3014 (1993).

Makeh et al., "Analysis of a brain–specific isozyme. Expression and chromatin structure of the rat aldolase C gene and transgenes" *J. Biol. Chem.,* 269:4194–4200 (1994).

Makino et al., "Cloning and characterization of a c–myc intron binding protein (MIBP1)" *Nuc. Acids. Res.,* 22:5679–5685 (1994).

Maniatis et al., "Regulation of inducible and tissue–specific gene expression" *Science,* 236:1237–1245 (1987).

Sauerwald et al., "The 5' –flanking region of the synapsin I gene" *J. Biol. Chem.,* 265:14932–14937 (1990).

Van Thai et al., "Identification of a neuron–specific promoter of human aromatic L–amino acid decarboxylase gene" *Mol. Brain Res.,* 17:227–238 (1993).

Becker et al., "Use of recombinant adenovirus for metabolic engineering of mammalian cells" *Methods in Cell Biology,* 43:161–189 (1994).

Bett et al., "An efficient and flexible system for construction of adenovirus vectors . . . " *Proceedings of the National Academy of Sciences USA,* 91:8802–8806 (1994).

Krougliak and Graham, "Development of cell lines capable of complementing E1, E4 and protein IX . . . " *Human Gene Therapy,* 6:1575–1587 (1995).

Morsy et al., "Efficient adenoviral vector mediated ornithine transcarbamylase expression in deficient mouse . . . " *J of Clinical Investigation,* 92:1580–1586 (1993).

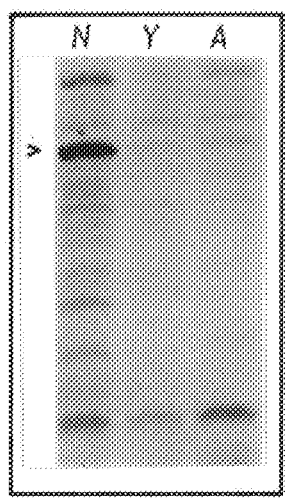
Fig-1
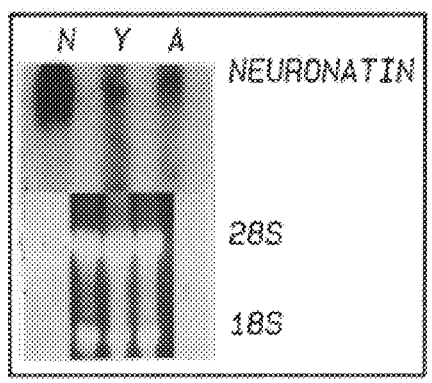
Fig-2
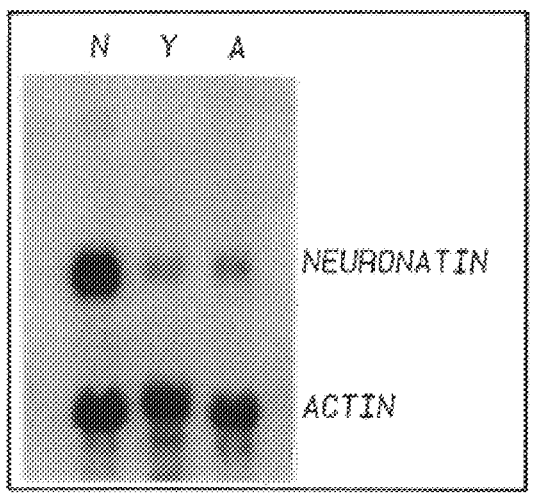
Fig-4
```
    40 —— NcoI
   112 —— PstI
   214 —— PstI
   511 —— NcoI
   556 —— XhoI
   633 —— NcoI
   925 —— BamHI
  1160 —— PstI
  1195 ——
```
Fig-3

```
GCGAACCCTTGCTCTCGACCACCCACCCACTTTCGGAACCATGGCCGCAGTGGCAGCAGCCTCGG    25
                                    M  A  A  V  A  A  A  S

CAGAACTGCTCATCATCGGCTGGTACATCTTCCGCGTGCTGCTGCAGGTGTTCAGGTACTCCCTG    90
 A  E  L  L  I  I  G  W  Y  I  F  R  V  L  L  Q  V  F  R  Y  S  L
```

GTGTTCCTGGAATGCTGCATTTACTGGGTAGGATTCGCTTTTCGAAATCCTCCAGGGACACAGCC
 V  F  L  E  C  C  I  Y  W  V  G  F  A  F  R  N  P  P  G  T  Q  P
CATTGCGAGAAGTGAG
 I  A  R  S  E

```
CAGAAGCTGGCGCACACGGTGTCCCGGACCGGGCGGCAGGTGCTGGGGGAGCGCAGGCACCGAGC   155
 Q  K  L  A  H  T  V  S  R  T  G  R  Q  V  L  G  E  R  R  H  R  A

CCCCAACTGAGGCCCCATCTCCCAGCCCTGGGCGGCCGTGTCATCAGGTGCTCCTGTGCTTCTCG   220
 P  N

ACCAGCATGGGAGCCAATGCCGCGCAGGAATGGGGGGTCCCCTGTGCTCCCTCGTCAGAGGAGCA   285
CTTGCCAAGGTCAGTGAGGGGCCGGTAGGTCCCCAGAAAAGCAGCACCGACAATGATGAAGACAT   350
CAGTTCCTTTCCCAGCCCCCCCCCCTTTGCCCCTGTCCCATGGCCGGCGGGTGGGAGAGGATGG   415
GGGAAGAGGGGAGCAACCCTCGAGATATGGGCGTAGCACCACATTCTGATCTGGACCAAGTTGG   480
AACAGCACCATCTCAGCCGCACAGATCCTACCATGGAGAGCTAACACCCCACCAACCAGCAGAAT   545
GGACATTCTGACATCACCAGCTGAAACCCTGAATCTCGGTGCAGAAGAGAAAGTGTCAACTGCGT   610
GCAGCACTGGGGGAGTGGAGGGTGTGGGTGGTGGAGGAAGAGGGTTAAGAAAACTAGTGGGGCCC   675
TCTTGCTGTCCCTTGCCTATGGCACGCATATTCCTGCCTTGCTCCCTCACTCCCCCTCTCCCCTG   740
CCTTCCAAAGCCCCACCCCCCAAAAATGTGTCACTTGATTCGGACCTATTCAACCAGTAATTGGA   805
TCCCACCTTTACCAAAACACCGTCTCTGACCCCCGGCCCTTCACTGATCTTGCTTATCCCTGGTC   870
TCACGCAGCAGTTGTGGTTGCTATTGTGGTAGTCGCTAATTGTACTAGTTTACGTGTGCATTAGT   935
TGTGTCTCCCCGGCTAGATTGTAAGCTCCTGGAGACAGGGACCACCTCCACAAAAAATAAAAAAA   1000
CGGACCTCTCCTGTCTTGTAGTGTGCTAGGACCCTGCAGGGCAGTGGGGTGCACCA             1057
```

*Fig-8*

-1300
GGATCCTGAG GCAGCTACAG CCTCGAAATA TTTTAAGATG GCAGCCTAGG

-1250
CTAAGCTTGC CTTTTTCAAA CAGCCCAGCG TCACTTTGCC AGAATCTGCC

AACTTCTCCG AAAGTCAATG TAGAAAAAAA GTCACTATGC TACTTTGTCC

AAACTGAACT CGTTTGGATC ATTACACCTC CATCTGCTGC TGGCACTGTA

CAGAACCTGA CCTCTGGGAG CTTTTAATGA AAATTAATTT TCTATCCACA

TAGGGGCAAA TGCCAGTTGG TCCCTGGGCC AGGCAGCTTG CTGGAAAGAG

-1000
GTGCTTTCGG CTAGCTACCG GTGCGCGGGG ACCACACTCA CAAACCGCAT

-950
TCCGGTCTTC CCGCCCGAAA ATCCGCGCTG TGCGAGGGAC CACAAGACT
           SP-1

-900
GGCGGTCTAA AAGGGACCCG CCTCACTTGG AAACGGGGCT GCGGTAGCAC

AACCCTCCGG TAGCGGTAGG TAACCCCGTT CGGTGATCCA GCCGCACAGC

-800
GCAACGGGTA CAAAGAACCC CACTGGCTAA GGCCGACCTA CCAGGGCTTG

-750
GGGGAGGGGA GCGGAAGACT GAGGTCGAAA CGACCTGTCC AGCAGAAAAC
AP-2                 δ Subunit

-700
TATCCCCAAG CATATTCCAA CCACTTCTCC GTAGAGCTCA TTCCTTCCGT

GCATACGAAG GGCGCCAATC CTTCCTGTAT CCCTCCCACA GTACCGGGTG

-600
ACTACTGCTT TTGCGCCCAA AGCGCAGTGC TCTGGCTCAG CTCCCTACAG

-550
TAGCGACCTC CACCGCAGAT TCTCATCTCC TCGCTACCGT AAGAGAGATG
          SRE-2

*Fig–10a*

```
                    -500
      TAAAGAATCA GACGGGTTAC GCGCTCAGGC ACCCTCATGA AGCAGAGGAC

-450
      CTGGGCTTAA AACTCATTCA GTATTAGGAA AAGAGCG CCGAGCACGGGCC
                         NRSE

-400
      TATTATGCCA AAGCTTCTGA AAGGGGCACC ACGTTTTTG CTCTATGGGG

-350
      CAGATGACCC CTCCCTAATT TCGTTTTCC ATCCATCCCC AAGGTAGGCT
              AP-2

-300
      TTGGAGTGGC ACCGGAGACT GAGCTCAAAT TTGCAGGCCA GGGACTGGGG
                                            NF-A1

AGAAGGGCGC CACACTAAGA GACCTGCACC CCCATTCTCG CCCTGTACTC

-200
      TACCCAGAGT CGTGGTACCC CTCCATTTTA AGCAAAATC CAAAAGCAAG

-150                                      -100
      TCTTCTGGAA GGGGGCTAAG ATGGAACTCA GGAGGCGGGG GTCGGTATGG

-50
      AAAGAGCAGA TGGATTATTT TTTTCCTCTC CTGGCGAATG AGGAGCGCCC
                           ETS            CAAT Box

+1
      CCAGCCACCC CTCCTCATAA ACACCCCCA AGGCGCGCAT GCGCACTTAG
                  TA Box                             ↘
                                                   mRNA Cap Site

GTGGCGGGCG GGTACTTAAG GCGCGGCCAC CGGGCTGGCA GTGCGCCCAA

+100
      CAGCGGACTC CGAGACCAGC GGATCTCGGC AAACCCTCTT TCTCGACCAC
                                                       ↓

+150
      CCACCTACCA TTCTTGGAAC C ATG GCG GCA GTG GCG GCG GCC TCG GCT GAA
                             Met Ala Ala Val Ala Ala Ala Ser Ala Glu
```

*Fig-10b*

CTG CTC ATC ATC GGC TGG TAC ATC TTC CGC GTG CTG CTG CAG
Leu Leu Ile Ile Gly Trp Tyr Ile Phe Arg Val Leu Leu Gln

GTAAGTC TGACGGGGTT TCGGGTTTCG GGTGGGATAG GGTTCCCAAC

TCGCGCCCCT AGAACCCGCA AGACTGCGTC GCGATTGCCG CTTCCCGGAC

CCGTCCTATT CCGATTGCCG CGATCCTTGC CTGCCCTTGT GCCGCTGCCG

GCACCGCGCG CCCCCTGCCC ATTCCCTGCG CCGTCCTCCT CGCGCTGACC

CTCCCTAGTG CGCCCGCGCC TGCCAGGGAA CAAAGACTCG GGGCGCGGCG

GGCGACCGCT GCGGACGATC ACCCAGGCAT TTAGCGACCT ACGCGGTAAG

+500
AAAAACCCGC TACACCCGGA CTCGACCCCA GGAGGGAGGC GGGGCACTAC
                                                             SP-1

+550
TGTGTTGAAA GACTTTACAG CTCGCAGAGT GAAAATTTTC CACCTTAAAA
                                                          AP-3

AATTGCGCAT TGCGGAGAAA TTTTATTTAA AAAAACATAT AGCGCTTGCG

GGGGTGGAAC AAAAAATAAG TTAGAAAAAG GCACTTCTCA GAAAAAATAA

AAATTACTTC GCAAAAAAAA AAAAAACCCT ACAACGAATT AGAGAAAAAG

TAGTTCACAC CAAAACAGAA AAACGCGCAT TGCAGGAAAA ATAAATCGGA

GAAAAGCACT TGGCAGAAAA AAATGCATTA GATTAAAAAC GCACTGCAGA

AAAAAATTAG ACAAGGGAGC TAACGGAAAA AAATGGATCG GGCCAAAAAC

GCTTTAAAGA AAAAAATTAG AGGAAAAAGC CCCTCGCGCG AAAAATAGAA

GGGGAAAAAA AGCACTTCCA AAAAGGACA ATTGCTTTAC AAAAAAAAA

AATAATAATA AAAAAAAATA AAAAGAGGC AAAAGCGCTT GGTGTAAAAA

GAGATAAATC AGAAGAAAGC GCTTTGCCCA TAAAATCATT TACCCTAAAA
                  ↓

*Fig-10c*

GCTCCCTTTG CAGGAAGAAT TCCCTGCTAA AGGAATCCTT TGCCAAAGGA

ATCGCATATT TCCTTCAAG GTG TTC CTG GAA TGC TGC ATT TAC TGG
↓                      Val Phe Leu Glu Cys Cys Ile Tyr Trp

GTA GGA TTC GCT TTT CGA AAT CCT CCA GGG ACA CAG CCC ATT
Val Gly Phe Ala Phe Arg Asn Pro Pro Gly Thr Gln Pro Ile

GCG AGA AGT GAG GTATACCTAA GTTGTGGGTC AATCAGCTT GCCGCCATGC
Ala Arg Ser Glu

AGCTCTCAGC ACAGTTGGAA AAGCTCCAGC TGCCCTGACT CGTGGACAAC

TGCGCCCGCG CCCCGCCTCT CCAGCCTACG CTGAGTGGGC GGGCGGGGCA
                                                                ↓

GGGGGTGGGG CGGGGGTGGG CACGGCAGCA CCACAGACAT GCTGTGGGTG

CTATCCACTA AGGGTGGGTC CTGGGTTTCT CGTCGCAG GTG TTC AGG
                                                               Val Phe Arg

TAC TCC CTG CAG AAG CTG GCA TAC ACG GTG TCG CGG ACC GGG CGG
Tyr Ser Leu Gln Lys Leu Ala Tyr Thr Val Ser Arg Thr Gly Arg

CAG GTG TTG GGG GAG CGC AGG CAG CGA GCC CCC AAC TG AGGCCCAGC
Gln Val Leu Gly Glu Arg Arg Gln Arg Ala Pro Asn

TCCCAGCCCT GGGCGGCCGT ATCATCAGGT GCTCCTGTGC ATCTCGGCCA

GCACGGGAGC CAGTGCCGCG CAGGAATGTG GGGTCCCCTG TGTTCCCTCG

CCAGAGCACT TGGCAAGGTC AGTGAGGGGC CAGTAGACCC CCGGAGAAGC

AGTACCGACA ATGACGAAGA TACCAGATCC CTTCCCAACC CCTTTGCACC

GGTCCCACTA AGGGGCAGGG TCGAGAGAGG AGGGGGGATA GGGGGAGCAG

ACCCTGAGAT CTGGGCATAG GCACCGCATT CTGATCTGGA CAAAGTCGGG

ACAGCACCAT CCCAGCCCCG AAGCCCGGGC CATGCCAGCA GGCCCCACCA

TGGAAATCAA AACACCGCAC CAGCCAGCAG AATGGACATT CTGACATCGC

*Fig-10d*

CAGCCGACGC CCTGAATCTT GGTGCAGCAC CCACCGCGTG CCTGTGTGGC

GGGACTGGAG GGCACAGTTG AGGAAGGAGG GTGGTTAAGA AATACAGTGG

GGCCCTCTCG CTGTCCCTTG CCCAGGGCAC TTGTATTCCA GCCTCGCTGC

ATTTGCTCTC TCGATTGCCC CTTTCCTCCT ACATGCCTCC CAAGCCCACC

CTACTCCAAA AGTAATGTGT CACTTGATTT GGAACTATTC AAGCAGTAAA

AGTAAATGAA TCCCACCTTT ACTAAAACAC TTTCTCTGAA CCCCCCTTGC

CCCTCACTGA TCTTGCTTTT CCCTGGTCTC AGCAGTTGTG GTCAATATTG

TGGTAATCGC TAATTGTACT GATTGTTTAA GTGTGCATTA GTTGTCTCTC

+2400
CCCAGCTAGA TTGTAAGCTC CTGGAGGACA GGGACCACCT

CTACAAAAAA TAAAAAAAGT ACCTCCCCTG TCTCGCACAG TGTCCCAGGA
　　　　Poly(A) Signal

+2500
CCCTGCGGTG CAGTAGAGGC GCACCAAAAC TTTGTCTCTT GTGATTTCTT
　　　　Poly(A) Site　　┤　　　　　　GT Cluster

+2550
TAGCGGCATC AACATACACT TCTAAGACTC AGCTGATGTG CCCACTGTGG

AACAGGCACA CTGCTTGGGG GAGGGAGGAA AAGGAGGGCC ATCAAAATTG

+2650
CAATAAGCTG GGCCCCTCAC ACACCCAACC CCATCTCAAT GCTGTCCTGT GAT

*Fig-10e*

NEURONAL-NEONATAL GENE: NEURONATIN

This application is a continuation-in-part of U.S. Pat. Ser. No. 08/259,299 filed Jun. 13, 1994, now abandoned.

GRANT REFERENCE

Research in this application was supported in part by grants from the National Institutes of Health (NS-01521) and the American Heart Association-National Center (92-13200). The Government and the American Heart Association, Inc. have certain rights in the invention.

BACKGROUND OF THE INVENTION

1. Technical Field

A DNA sequence which encodes a vertebrate neuron-specific mRNA and which can be used to screen for genetic defects and can be used in neural regeneration.

2. Background Art

Human developmental disorders such as microencephaly and lissencephaly result from abnormal brain growth. Abnormalities in human brain development are seen in 75% of fetal deaths and in 40% of deaths during the first year of life. About 3% of all births have major brain or systemic defects, and 5–15% of pediatric neurology admissions are primarily related to craniospinal malformations. Although the cause is not known in 60% of the cases, chromosomal factors are known to be responsible in at least 6% of the cases. Therefore, it is critical to elucidate the molecular controls that may be amenable to iatrogenic regulation during human brain development. The later phases of mammalian brain development is characterized by rapid neuronal proliferation in the subventricular zone and their migration along radial glial fibers into the more superficial layers of the brain. This process results in rapid brain growth and accounts for much of the subsequent gain in brain weight. Therefore, it is not surprising that abnormalities of neuronal proliferation and migration lead to profound developmental retardation manifesting principally as microcephaly.

An abnormally small brain may result from either genetic abnormalities or from an insult, such as exposure to alcohol, incurred during the later stages of gestation. At birth, the brain may weigh as little as 500 gms and resemble that of a 3–5 month old fetus. There are several neuronal proliferation and migration disorders, including lissencephaly, schizencephaly, macrogyria, micropolygyria, agenesis of the corpus callosum and gray matter heterotopias. Besides mental retardation, about 33% of these children suffer seizures.[20]

When there are miscarriages or birth defects due to abnormalities in brain development such as microencephaly and lissencephaly, families need counseling as to the cause and possibility of reoccurrence. (See Gelehrter & Collins *Principals of Medical Genetics*, Williams & Wilkins, 1990 for a general discussion of genetic counseling.)

Rapid brain growth due to a surge in neuronal proliferation and migration is a characteristic feature of the later stages of mammalian fetal development. Following the closure of the neural tube, waves of neuroblasts originating in the neuroepithelium of the ventricular zone migrate into the superficial marginal zone.[30] Although neuronal proliferation begins at embryonic day 12–13 (E12–13) in the rat, the process accelerates later in development and continues into the neonatal period accounting for much of the subsequent gain in brain weight.[35] In the human brain, rapid neuronal proliferation and migration begins at about 8–10 weeks after fertilization and accounts for much of the expansion in brain volume and weight seen between 14 and 38 weeks of gestation.

It would be useful to be able to monitor brain growth during these early stages. For example, it would be useful to know if a miscarriage or neurologic birth defect were due to abnormal brain growth and/or neuronal migration so that families could be properly counseled. It would also be useful to be able to test fetal development in utero for pregnancies at risk of abnormal brain growth and/or neuronal migration.

Fetal brain cell transplantation has shown some promise in the treatment of Parkinson's Disease and has been suggested for Alzheimer's. Results similar to those seen with Parkinson's disease have been obtained in tissue transplantation models for Huntington's disease, amyotrophic lateral sclerosis (ALS) and hereditary ataxia. Transfer of genetically engineered cells may also allow for specific manipulation of the brain microenvironment in Alzheimer's disease as well.[12] As transplantation of fetal neural tissue is explored it would be useful to be able to monitor the tissue to determine if it was properly developing.

Most physiological functions decline with age. However, the rate and extent of decline varies with tissue. Aging severely affects the nervous system and, in particular, the neurons. The senile dement exhibits superficial resemblance to the helpless young child. Between the 3rd and 10th decade of life, the average weight of the brain declines by 233 grams.[1,17,18] The cause for this is presumably neuronal degeneration and replacement gliosis.[19] Large neurons (>90 $\mu$M) in the midfrontal, superior temporal, and inferior parietal areas of the neocortex show a strong negative correlation with age. Small neurons (40–90 $\mu$m) and glial cells increase with age.

The loss of neurons is most marked after the 7th decade of life. Over 25% of hippocampal neurons are lost between the ages of 45 and 95 years of age.[2] It was thought that aging also resulted in loss of neuronal dendrites,[60] but this is controversial.[4] These morphological changes may underlie age-associated memory impairment and learning disabilities and an ultimate failure of neurons to function.[13]

Further, age may govern the ability of neurons to resist injury. For example, it is well known that to establish neurons in culture, embryonic brain needs to be used, the adult brain is nearly useless for this purpose. Anecdotal accounts of infants and children being able to withstand hypoxic injury, such as in drowning accidents, better than adults is indirect support for this belief. Further analysis along these lines highlights another obvious difference between the developing and adult brain. The developing neuron grows, but the adult neuron does not. As the genes themselves are largely unchanged during development, the basis for these differences in embryonic and adult brain must involve differential gene expression.

It would, therefore, be useful to be able to regenerate neurons, not only in aging, but in degenerative diseases that involve the loss of neurons. It appears that development culminates in progressive loss of function, degeneration and death of even normal neurons. In certain neurodegenerative conditions such as Huntington's disease, Alzheimer's disease and Parkinson's disease this process of degeneration is more marked in certain neurologic subpopulations. Although the precise molecular mechanism for failure of growth in adult neurons is unclear, there clearly is a strong basis to transfer developmental genes involved in brain growth into adult neurons to rekindle generation, i.e. reestablish a fetal stage.

Aging culminates in total failure of cells to divide and function. Nevertheless, only a small percentage of the population die of normal aging alone. Most die of diseases to which they are increasingly susceptible by the aging process. However, even if the major diseases causing death in the elderly such as coronary artery disease and cancer are eliminated, life expectancy will be increased only by about 3 and 2.5 years respectively.[34]

Hayflick and Moorhead observed that fibroblasts divide only a fixed number of times (population doubling times).[26] Human infant fibroblasts divide about 50 times, those of a 20-year old man about 30 times, and those of a 80-year old about 20 times.[27] A large number of studies have used aging fibroblasts in culture as a model for studying the molecular mechanisms of aging. With increasing age, cellular macromolecules progressively accumulate errors, such as mutations,[14] telomere shortening,[24] DNA hypomethylation,[5] impaired DNA repair,[54] protein cross linking[69] and decreased protein degradation.[50,16] However, the mechanisms by which these changes may be involved in senescence remain unclear. The inevitable progression of development into senescence is likely to involve changes in gene expression manifesting either as upregulation or downregulation of genes, or both.[39]

Although there is an overall reduction in total RNA production during senescence,[63,56] the rate and stability of brain mRNA synthesis are unchanged compared to younger tissue.[11] In hybrids constructed using senescent and young fibroblasts, the senescent phenotype is dominant.[53] The factors responsible for this dominance may involve genes that are known to be overexpressed[15,45,46] or underexpressed[61,62] in senescent cells. Senescent cells exhibit defective transcription of c-fos,[61] needed for the initiation of DNA synthesis. Furthermore, posttranslational modification of c-fos is dysfunctional resulting in impaired binding with c-jun to form AP-1 transcription factor complex.[55] Cell-cycle control genes, cdc2 and cyclins A and B either exhibit low levels or impaired function in aging cells.[62,47] In particular, senescent cells exhibiting low cdc2 gene product fails to phosphorylate RB protein. Ornithine decarboxylase mRNA is reduced in aging cells, its translation impaired, and its protein rapidly degraded.[6] Aging cells also exhibit expression of statin and terminin, two proteins that are specifically induced during aging, possibly due to impaired lysosomal proteolysis.[66,67]

Yeast is another model for aging. Jazwinski et al. have identified several genes that are differentially expressed in young and aged yeast cells.[31] Aging yeast do not express ras-2 protein involved in signal transduction and growth. They also fail to express lag-1 gene. Interestingly, overexpression of lag-1 increases life span by about 30%. Similar results have also been observed in *Drosophila melanogaster*. More recently, heritable variation in rates of senescence within a population of Drosophila have been demonstrated.[29]

SUMMARY OF THE INVENTION AND ADVANTAGES

According to the present invention, an isolated and purified DNA sequence which encodes a vertebrate mRNA for a neuron specific protein, neuronatin, is disclosed. The mRNA is expressed in brain tissue during rapid brain growth when there is a surge in neuronal proliferation and migration. In the human the genomic DNA is as set forth in SEQ ID No:6 and the cDNA has a nucleotide sequence as set forth in SEQ ID No:5. The organization of human neuronatin gene and its mapping to human chromosome 20q11.2–12 is set forth. The mRNA encodes an amphipathic polypeptide that exhibits homology, both in its primary and secondary structure to a proteolipid class of proteins which function as regulatory subunits of ion channels.

The present invention also includes a rat cDNA having a nucleotide sequence as set forth in SEQ ID No:1, designated neuronatin-α and a rat cDNA having a nucleotide sequence as set forth in SEQ ID No:2, designated neuronatin-β.

The present invention also includes a neuronatin protein that is deduced as 9.2 kD with a highly hydrophobic N-terminal arranged in an α-helix and a hydrophilic C-terminal. In the rat, neuronatin-α has an amino acid sequence as set forth in SEQ ID No:3 and neuronatin-β as set forth in SEQ ID No:4.

The present invention further includes an antibody directed against the neuronatin protein which can be conjugated to a detectable moiety. The present invention also includes neuronatin genomic DNA and cDNA constructs.

The present invention provides methods of screening for neuronatin protein, mRNA and DNA. Further methods of screening for neuronatin genetic defects in fetal tissue prior to transplantation or for identifying carriers of genetic defects for genetic counseling are disclosed. A kit for detecting the neuronatin genetic abnormalities is also disclosed.

The present invention provides a method of reestablishing a fetal level of neuronatin mRNA expression in post-mitotic neurons. Gene transfer of the coding sequence of neuronatin cDNA and/or DNA into postmitotic neurons is undertaken using the replication-defective retroviral vector, pLXSN.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a photograph of a differential display gel of brain cDNA from healthy 3 day old (neonate (N)), 3 month old (young adult (Y)) and 33 month old (aged adult (A)) male Fischer 344 rats, the cDNA fragment is shown at the arrowhead;

FIG. 2 is a photograph of Northern hybridization gel of brain RNA from neonatal (N), young adult (Y), and aged adult (A) rats using the cDNA fragment extracted from the differential display gel as the probe (FIG. 1) and ethidium bromide stained gels pictured under UV light prior to transfer showing that similar amounts of RNA were applied;

FIG. 3 is a restriction map of neuronatin;

FIG. 4 is a photograph of Northern hybridization gels of neonatal rat brain (N), young adult brain (Y) and aged rat brain (A) using the full length cDNA sequence (SEQ ID No:1) for neuronatin-α, as the probe;

FIG. 8 is the sequence for the two alternatively spliced forms of rat neuronatin cDNA, Neuronatin-α (three exons) and Neuronatin-β (two exons) (middle exon (box) spliced out), the middle exon exhibits prototypical features of an intron, including consensus GT-AG and a branch site, TCGAAAT, located 33nt upstream of the 3'-end underlined, and translation start (GAACCATGG), stop (TGA) and termination (AATAAA followed by CA) signals are also underlined, poly(A) tail began at position 1057;

FIG. 10 is the complete human neuronatin gene sequence wherein nucleotide numbering begins at the 5'-end of the first exon (transcription start site), regions exhibiting homology to consensus sites for transcription factors, SP-1, AP-2 (two sites), δ-subunit, SRE-2, NRSE, NF-A1 and ETS within the 5'-flanking region, SP-1 and AP-3 within intron-1, and modified CAAT and TATA boxes are underlined, the transcription start site is indicated by a thick horizontal arrow, the exon/intron boundaries are indicated by vertical arrows, the coding regions of the three exons and their deduced amino acid sequences are shown using the three-letter-code, the translation initiation site, stop signal, poly (A) signal, poly(A, site and GT cluster are also underlined.

DETAILED DESCRIPTION OF THE PREFERRED EMBODIMENT

Figure 5:
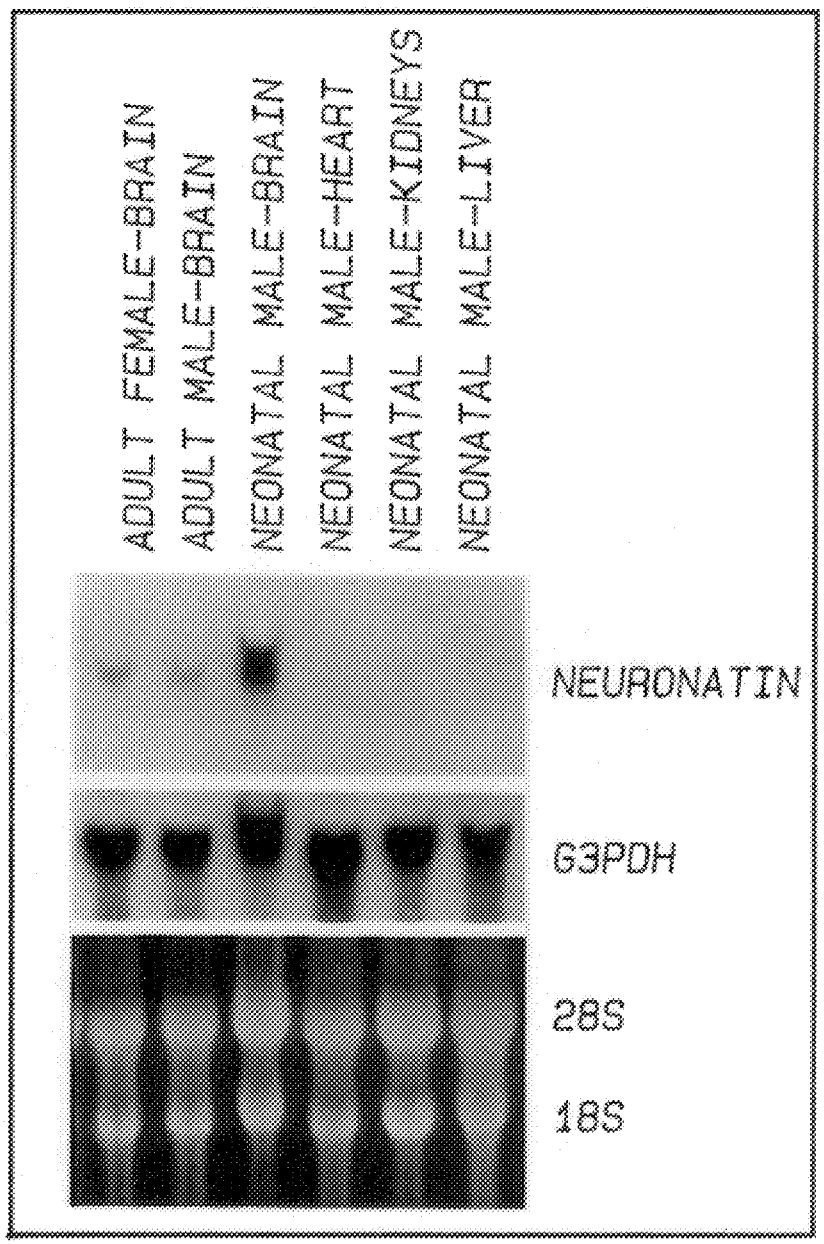
FIG. 5 is a photograph of Northern hybridization gels for differential age and tissue expression of neuronatin mRNA in F344 rats, bottom panel ethidium bromide staining photographed under UV light, middle panel blot after being stripped and rehybridized with human glyceraldehyde-3 phosphate dehydrogenase (G3PDH) and top panel hybridized with $^{32}$P-labelled neuronatin-α cDNA.

The present invention provides an isolated and purified rat cDNA (SEQ ID Nos:1–2) and human cDNA (SEQ ID No:5) for a novel protein, neuronatin, that is found in brain tissue during rapid brain growth when there is a surge in neuronal proliferation and migration during the later stages of mammalian fetal development. Neuronatin has a role in brain development and differentiation due to its abundant mRNA expression during late fetal and early postnatal periods of mammalian brain development, and downregulation during adulthood and senescence. Downregulation of mRNA production correlated with brain differentiation. The pattern of mRNA expression seen in human fetal and adult brain also suggests that neuronatin is highly expressed during a period of human fetal brain development (18–24 weeks), when brain growth is rapid. With onset of differentiation and maturation, neuronatin expression declines.

There are two forms of neuronatin proteins, α (SEQ ID No:3) and β (SEQ ID No:4) known in the rat and at least one neuronatin protein in the human. Further, the present invention provides the isolated and purified human genomic DNA (SEQ ID No:6) and polymorphisms thereof specific for neuronatin. By "isolated" is meant separated from other nucleic acids found in humans. By "specific" is meant an isolated sequence which encodes the protein neuronatin.

Modification to the nucleic acids of the invention are also contemplated as long as the essential structure and function of the polypeptide encoded by the nucleic acids are maintained. Likewise, fragments used as primers or probes can have substitutions as long as enough complementary bases exist for selective, specific hybridization with high stringency.

Polymorphisms are variants in the gene sequence. They can be sequence shifts found between different ethnic and geographic locations which, while having a different sequence, produce functionally equivalent gene products. Polymorisms also encompass variations which can be classified as alleles and/or mutations which can produce gene products which may have an altered function. Polymorisms also encompass variations which can be classified as alleles and/or mutations which either produce no gene product, an inactive gene product or increased levels of gene product.

Vectors have been prepared[48] as, for example, rat neuronatin-α cDNA has been cloned into the EcoRI site of pUC19 (pUC19.RNNα) and rat neuronatin-β is also cloned into EcoRI site of pUC19 (pUC19.RNNβ). The human neuronatin cDNA is cloned into pGEMZf (pGEMZf.HNN).

Sense and nonsense constructs of neuronatin are ligated into the replication-defective retroviral vector pLXSN and used to transfer the gene into NIH3T3 and LaN1 human neuroblastoma cells. Stable cell lines expressing the sense (NIH3T3.NNsense; LaN1.NNsense) and nonsense (NIH3T3.NNnonsense; LaN1.NNnonsense) constructs are established.

The present invention also provides an antibody that is specifically reactive with the neuronatin protein of both human and rat origin. "Specifically reactive" as used herein describes an antibody or other ligand that specifically binds the neuronatin protein and does not substantially crossreact with any antigen other than the neuronatin protein. Antibody can include antibody fragments such as Fab.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982.) The binding of antibodies to a solid support substrate is also well known in the art. (see for a general discussion Harlow & Lane *Antibodies: A Laboratory Manual*, Cold Spring Harbor Laboratory Publications, New York, 1988) The detectable moieties contemplated with the present invention can include, but are not limited to, fluorescent, metallic, enzymatic and radioactive markers such as biotin, gold, ferritin, alkaline phosphatase, β-galactosidase, peroxidase, urease, fluorescein, rhodamine, tritium, $^{14}C$ and iodination. In a preferred embodiment, β-galactosidase is used.

The present invention provides a method of monitoring for the presence of the protein neuronatin, neuronatin mRNA and the genomic DNA encoding neuronatin. Such screening is useful for genetic counseling and for fetal tissue transplantation.

When there are miscarriages or a birth defect in a proband due to abnormalities in brain development such as microencephaly and lissencephaly, families need counseling as to the cause and possibility of reoccurrence. In order to determine whether a genetic defect in the gene for neuronatin is involved, the proband must be screened for abnormal neuronatin activity, as well as the parents and/or siblings and possibly other family members, for the presence of a defective neuronatin gene.

To screen for the presence of neuronatin in the proband, specimens of fetal brain tissue, neonatal brain tissue, amniotic fluid, cerebrospinal fluid or chorionic villi are collected and assayed. The availability of a sample, type of sample and whether protein, mRNA or DNA are being measured will determine the assay to be used. Such principles are well known in the art and can be routinely determined by one who is skilled in the art. Since the protein has been shown to be neuronal specific, samples for direct protein and mRNA measurements are selected from brain tissue. Amniotic fluid and cerebrospinal fluid will have cells and/or proteins that are shed from the tissues they bathe. Chorionic villi, cells and tissue can all be screened for DNA.

Amniocentesis, chorionic villus sampling and spinal taps are well known to those skilled in the medical art. Brain tissue biopsies will generally be surgical biopsies or from autopsy material.

In the present invention the specimens are assayed for the protein utilizing assay systems that are standard in the art such as immunoassays including immunohistochemical and immunocytochemical staining, enzyme linked immuosorbent assays (ELISA), radioimmunoassays (RIA), immunoblot as well as Western blotting and immunoprecipitation.[57]

In a preferred embodiment, Western blotting will be used. Protein specimens will be electrophoresed on SDS-PAGE, electrotransferred and incubated with the specific antibody which in turn will be detected using a second antibody tagged with a suitable detectable moiety.

ELISAs are one immunoassays employed to assess the amount of neuronatin in a specimen. ELISA assays are well known to those skilled in the art. Both polyclonal and monoclonal antibodies can be used in the assays. Where appropriate other immunoassays, such as radioimmunoassays (RIA) can be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, *Molecular Cloning: A Laboratory Manual*, Cold Springs Harbor, New York, 1989.

Further, immunohistochemical staining is available to screen tissue sections for the presence of protein as well as immunocytochemical staining for isolated cells. (see Stites and Terr,*Basic and Clinical Immunology*, Appleton & Lange, 1991, for a general discussion of immunostaining.) Briefly, the tissue sections are fixed and sectioned generally in a freezing microtome. Sections are usually blocked in 20% normal rabbit serum (NRS) for 20 min, and then exposed for 60 min to the appropriate antibody as described above. The section is then usually fixed in 1% neutral formalin in PBS for 5 min, washed in PBS for 10 min, incubated for 60 min in FITC conjugated, or other conjugate suitable for immunohistochemistry, second antibody (diluted 1:500 in 10% NRS/2.5% BSA), and finally washed in PBS for 30 min. The entire staining procedure can generally be carried out at room temperature.

Alternatively, isolated cells can be washed in serum free media, blocked in 20% NRS in media for 15 min, exposed for 40 min to the appropriate antibody as described above, washed in Ca-Mg PBS, fixed with paraformaldehyde, washed in PBS for 20 min, incubated with a conjugated second antibody for 30 min, and finally washed in PBS for 30 min. Procedures up to fixation are generally carried out at 37° C., and thereafter at room temperature.

Alternatively the staining can be undertaken with an appropriate antibody conjugated to a detectable moiety as described above, though this does not generally give as intense staining as the use of a conjugated second antibody. The tissue sections or cells are examined after immunocytochemical staining by phase and fluorescence light microscopy.

The samples can be assayed for mRNA utilizing in situ hybridization,[43] Northern blotting and reverse transcriptase—polymerase chain reaction (RTPCR).[36] In the preferred embodiment Northern blotting as described and shown in the examples hereinbelow is used.

The samples can be assayed for DNA utilizing in situ hybridization,[43] Southern blotting,[57] single strand conformational polymorphism (SSCP)[51] and PCR amplification using neuronatin specific primers. In the preferred embodiment a Southern blotting assay is used. In general, the cell or tissue biopsy samples to be analyzed can be any cell type (except red blood cells) with lymphocytes or skin biopsies being the preferred cell type. Either chorionic villi or cells from amniotic fluid can be used for in utero analysis.

The present invention provides a method of screening fetal tissue for neuronatin genetic defects and of screening for potential carriers of the defect. The method provides for the identification of deletions, either partial, full or a frameshift mutation, of the DNA coding sequence of neuronatin and the detection of mutations, such as point mutations (missense and nonsense). Further, the method of the present invention allows for the identification of regulation defects.

The preferred method for identifying mutations in the DNA sequence is SSCP.[51] SSCP allows detection of conformational changes in DNA resulting from even single base substitutions.

Once the mutation in the DNA sequence has been identified in the proband, the family can be screened for the presence of the defect and future offspring can also be screened in utero.

The regulatory defects can be identified by the presence of a nonmutated DNA sequence for neuronatin coupled with the presence of neuronatin protein or mRNA in abnormal amounts or at an abnormal time or the absence of neuronatin at the required time in development. The presence of neuronatin can either be assayed directly or through mRNA detection.

The present invention also allows the screening of fetal tissue prior to transplantation for genetic defects. Abnormalities in human brain development are seen in 75% of fetal deaths and in 40% of deaths during the first year of life. Therefore, it is necessary to screen such tissue prior to use. The present invent-on provides a method of determining whether neuronatin levels of mRNA, protein and the DNA sequence are normal and therefore suitable for transplantation. (For a general discussion of fetal transplant see *Functional Neural Transplantation*, Dunnett and Björklund, editors, Raven Press, 1994)

Further, it is envisioned that the present invention provides a kit for screening fetal tissue for genetic defects and screening for genetic counseling. The kit includes controls for normal human neuronatin in the form of either neuronatin genomic DNA sequences, neuronatin cDNA, neuronatin protein and mRNA depending on the assay to be preformed. The kit will also include neuronatin specific primers needed for PCR amplification based assays that will allow detection of both quantitative and qualitative abnormalities in the neuronatin gene and specific antibodies for neuronatin. The antibodies will be tagged with a detectable moiety depending on the assay to be performed with the kit.

The present invention provides a method of reestablishing a fetal stage in neurons by reinitiating neuronatin mRNA synthesis. The present invention contemplates gene transfer of the coding sequence of neuronatin cDNA and/or genomic DNA into postmitotic neurons using vectors.[138,139,140,141]

Such vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses and retroviruses, DNA viruses, cosmids, plasmids, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York (1989, 1992), in Ausubel et al., *Current Protocols in Molecular Biology*, John Wiley and Sons, Baltimore, Md. (1989), Chang et al., *Somatic Gene Therapy*, CRC Press, Ann Arbor, Mich. (1995), Vega et al., *Gene Targeting*, CRC Press, Ann Arbor, Mich. (1995), Vectors: *A Survey of Molecular Cloning Vectors and Their Uses, Butterworths*, Boston Mass. (1988) and Gilboa et al (1986) and include, for example, stable or transient transfection, lipofection, electroporation and infection with recombinant viral vectors. Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

In one embodiment the replication-defective retroviral vectror, pLXSN, is used. In a further embodiment a neuron specific retrovirus carrier can be used to specifically target the neurons in a living organism.

In a further embodiment the DNA viral vector for introducing and expressing recombinant sequences is the adenovirus derived vector Adenop53TK. This vector expresses a herpes virus thymidine kinase (TK) gene for either positive or negative selection and an express on cassette for desired recombinant sequences. This vector can be used to infect cells that have an adenovirus receptor which includes neuronal cells. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recomnbinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

An alternate mode of administration is by direct inoculation locally at the site of the disease or pathological condition or by inoculation into the vascular system supplying the tumor with nutrients. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes can also be used to introduce the non-viral vectors described above into recipient cells within the inoculated area. Such transfection vehicles are known by one skilled within the art.

The present invention provides for transgenic neuronatin gene and polymorphic neuronatin gene animal and cellular (cell lines) models as well as for knockout neuronatin models. These models are constructed using standard methods known in the art and as set forth in U.S. Pat. Nos. 5,387,742, 5,360,735, 5,347,075, 5,298,422, 5,288,846, 5,221,778, 5,175,385, 5,175,384, 5,175,383, 4,736,866 as well as Burke and Olson, (1991), Capecchi, (1989), Davies et al., (1992), Dickinson et al., (1993), Huxley et al., (1991), Jakobovits et al., (1993), Lamb et al., (1993), Rothstein, (1991), Schedl et al., (1993), Strauss et al., (1993). Further, patent applications WO 94/23049, WO 93/14200, WO 94/06908, WO 94/28123 also provide information.

The present invention was developed by extracting total RNA from neonatal, young adult and aged rat brain and processed for differential display. A cDNA fragment selectively expressed in neonatal brain was identified (FIG. 1). This cDNA fragment was extracted from the gel, PCR-amplified and confirmed on Northern blot to be selectively expressed in the neonatal brain (FIG. 2). The mRNA was estimated to be about 1.2 kb.

The cDNA fragment was cloned and sequenced (SEQ ID Nos:18–22). As there was no homology for this sequence in GenBank, applicants used this cDNA fragment to screen a λgt 11 cDNA library prepared from the same sample of brain RNA. Of the nine positive clones identified, one clone contained an insert matching the size of the detected mRNA species. This insert was fully sequenced in both directions.

The rat full length sequence was 1195 bp long (neuronatin-α; SEQ ID No:1), has three exons and had no homology in GenBank (GenBank Accession number U08290). Although the 3'-untranslated region of the neuronatin-α sequence matched with part of the 3'-untranslated region of calbindin-D28K,[26] the entire 5'-untranslated region and first 208 nt (out of 243 nt) of the coding region were unique, i.e. were nonhomologus and unrelated to calbindin-D28k. (Table 1) An alternatively spliced sequence, neuronatin-β was also found which has only two of the three exons in neuronatin-a and had no homology in GenBank (GenBank accession number U09785).

The sequence (SEQ ID No:1) has a strong translation initiation site GAACCATGG[38] and a coding region for 81 amino acids from nt 41 to 283 followed by the stop signal. The deduced protein of the full length sequence (neuronatin-α; SEQ ID No:3) is novel having no homologous sequences in the database. The 3'-untranslated region was 912 nt long with the prototypical termination signals AATAAA located at position 1112, CA at position 1174 followed by the poly(A) tail beginning at position 1178.[65] The restriction map was generated (FIG. 3) with digestion with six enzymes, EcoRI, NotI, PstI, BamHI, NcoI and XhoI. There were no sites for EcoRI and NotI.

TABLE 1

|  | Neuronatin-α | Calbindin-D28k |
|---|---|---|
| Locus | RNU08290 | RATCALBDF |
| GenBank accession no. | U08290 | M27839 |
| Total cDNA length (bp) | 1195 | 3352 |
| Location of coding region | 41-283 | 628-1413 |
| Homology: |  |  |
| Region of interest | 1-1177 | 2160-3352 |
| No match | 1-208 | 2160-2380 |
| Additions |  | 2390(+C) |
|  | 242(+G) |  |
|  | 401(+G) |  |
|  | 434(+G) |  |
|  | 437(+C) |  |
|  | 438(+C) |  |

TABLE 1-continued

|  | Neuronatin-α | Calbindin-D28k |
|---|---|---|
|  |  | 2623(+G) |
|  |  | 2626(+C) |
|  |  | 2642(+C) |
|  |  | 2796(+A) |
|  |  | 2821(+C) |
|  |  | 2881(+G) |
| Substitutions | 810(T) | 2985(G) |
|  | 811(G) | 2986(T) |
|  | 1146(G) | 3321(C) |

The full length sequence (SEQ ID No:1) was used in Northern blotting to confirm selective expression in neonatal brain (FIGS. 4–8). Both forms of neuronatin cDNA hybridized to a mRNA species of 1.2 kb, so the α-form was used. Neuronatin was relatively selectively expressed in the brain, and not in the heart, kidney or liver or other tissues tested. Other investigators, using in situ hybridization techniques, noted neuronatin mRNA to be expressed in the developing hindbrain.[113] The appearance of neuronatin mRNA first in rhombomeres-3 and 5 of early embryonic mice suggests a role in hindbrain segmentation.

The expression of neuronatin actually appeared to precede visible morphological changes, again suggesting a mechanistic role. Clearly, more work needs to carried out to determine the specific mechanism by which neuronatin is involved in this process, and to understand the separate functions of neuronatin, Krox-20[114] and sek[100], the other genes noted to be selectively expressed in rhombomeres-3 and 5. One major difference, however, unlike Krox-20 and sek which are expressed only transiently during development, the expression of neuronatin becomes more generalized and abundant in the nervous system later in development. Based on these findings it appears that neuronatin is involved in determining segment identity in the hindbrain and in the maturation and maintenance of the post-mitotic neuronal fate.

When tested for hydropathy,[28] the protein (SEQ ID No:3) was highly hydrophobic from residues 1 to 36 with an α-helix and hydrophilic from residues 74 to 81 suggesting that the N-terminal may be membrane bound whereas the C-terminal was located in the cytoplasm.

In Northern blots using RNA from human brain, neuronatin mRNA was expressed in human fetal brain aged 18–24 weeks (FIG. 10) and sequenced (SEQ ID No:5). The genomic DNA has been sequenced (SEQ ID No:6) and the gene designated Neuronatin (nnn). The coding region for human neuronatin cDNA exhibits almost complete homology to rat neuronatin-β and is mapped to human chromosome 20q11.2–12.

Neuronatin mRNA is selectively expressed in the brain, but not in lung, liver and kidney, the other organs studied. Although, neuronatin mRNA was abundant in 18–24 week old human fetal brain, its expression was minimal in adulthood. When investigated further in the rat, neuronatin mRNA first appeared at E11–14, peaked at E16–19, and declined to baseline levels in adulthood. This close temporal association between the mRNA expression pattern of neuronatin and neurogenesis shows a functional relationship.

The deduced human polypeptide consists of two distinct domains on hydropathic analysis. The N-terminal was hydrophobic and arranged as a transmembrane α-helix, whereas, the C-terminal was hydrophilic and basic containing about 20% arginine residues. Neuronatin, both its amino acid sequence and secondary structure showed homology to two other genes, PMP1[98,99] and phospholamban[107], both polypeptides that function as subunits of cationtranslocating ATPases. The PMP1 gene product is a subunit of H+-ATPase and is a 40 amino acid peptide with an α-helix transmembrane domain and highly basic cytoplasmic domain. PMP1 modulates the activity of a plasma membrane proton pump by its association with H+-ATPase, the holoenzyme[97]. Functionally, deletion of PMP1 gene resulted in decreased H+-ATPase activity. Another protein showing a structural organization similar to that of human neuronatin protein is phospholamban[71,106]. Phospholamban is a 52 amino acid peptide[105] comparable in size to neuronatin. As with neuronatin and PMP1, phospholamban also has an α-helix transmembrane domain and a highly basic cytoplasmic domain that modulates the activity of $Ca^{2+}$-ATPase.

Neuronatin, PMP1 and phospholamban are amphipathic polypetides that are members of a class of proteins referred to as proteolipids (Table 2). Proteolipids are proteins that typically have two domains, one domain being hydrophobic and the other hydrophilic. Although, the primary amino acid sequences of the proteolipids are different, their structural organization is remarkably similar. The proteolipids are generally small polypeptides, fractionate into the chloroform/methanol phase and several members function as regulatory subunits of membrane channels. Other members of this class of proteins include γ-subunit, sarcolipin, PMP2, F-sub-c and vac-sub-c. The γ-subunit, a polypeptide of 58 amino acids, functions as a subunit of $Na^+/K^+$-ATPase[90]. Sarcolipin has 31 amino acids and functions as a subunit of $Ca^{2+}$-ATPase in skeletal sarcoplasmic reticulum[111]. PMP2 is highly homologous to PMP1, consists of 43 amino

TABLE 2

THE PROTEOLIPID FAMILY OF AMPHIPATHIC POLYPETIDES

|  | Amino Acids | Mol Wt (kDa) | Function | References |
| --- | --- | --- | --- | --- |
| Sarcolipin | 31 | 3.8 | $Ca^{2+}$-ATPase Skeletal Muscle | Wawrzynow et al 1992 |
| PMP1 | 40 | 4.7 | H+-ATPase Yeast | Navarre et al 1992 |
| PMP2 | 43 | 4.8 | H+-ATPase Yeast | Navarre et al 1994 |
| Phospholamban | 52 | 6.1 | $Ca^{2+}$-ATPase Cardiac Muscle | Tada 1991 |
| γ-Subunit | 58 | 6.5 | $Na^+/K^+$-ATPase | Mercer 1993 |
| Phospholemman | 72 | 8.4 | Choride Channel Taurine Channel | Palmer et al 1991 Moorman et al 1992, 1995 |
| F-sub-c | 75 | 7.6 | $F_1F_0$-ATPase Mitochondrial | Fearnley et al 1990 |
| Vac-sub-c | 155 | 15.8 | H+-ATPase Vacuolar | Mandel et al 1988 |
| Neuronatin | 54 | 6.2 |  |  | acids and functions as a subunit of yeast H+-ATPase[97]. F-sub-c is 75 amino acids long and is subunit-c of $F_1F_0$-ATPase[82]. Vac-sub-c contains 155 amino acids and constitutes subunit-c of vacuolar H+-ATPase[89]. Unlike these other, phospholemman, a 72 amino acid polypeptide,[101] is organized as a pentamer and functions as a novel chloride channel[94]. More recently, the phospholemman channel has also been shown to be selective for taurine[93]. Furthermore, proteolipids may also be involved in human disease. For example, F-sub-c is the major component of the storage organelles seen in neuronal ceroid lipofuscinosis[102], which is an autosomal-recessive lysosomal neurodegenerative condition of childhood manifesting as blindness, seizures, dementia and early death. The involvement of F-sub-c in the pathogenesis of this disease is supported by the finding that similar deposits occur in the mouse mutant, motor neuron degeneration (mnd/mnd), which is model for neuronal ceroid lipofuscinosis[81]. Neuronatin is a new member of the proteolipid family, and its unique expression only in the developing human brain, demonstrates that this gene be investigated is a novel membrane channel regulator during brain development.

With the help of human-rodent hybrid cell panel screening and fluorescence in situ hybridization, applicants mapped the neuronatin gene to human chromosome 20q11.2–12. The 20q11.2–12 region is rich in genes, including several involved in signal transduct ion and cell growth regulation. These include hemopoietic cell kinase (20q11–12)[104], Rous sarcoma protooncogene SRC (20q12–13)[96], phospholipase C (20q12–13.1), topoisomerase-I (20q12–13.1)[87], zinc finger protein 8 (20q13), CCAAT/enhancer binding protein (C/EBP) (20q13.1)[83], protein tyrosine phosphatase (20q13.1–13.2)[74], S-adenosyl homocysteine hydrolase (20cen-q13.1)[92] and potassium voltage gated channel (20q13.2). Although, there are no neurological conditions that are known to be mapped to 20q11.2–12, adjacent areas of chromosome-20 have been implicated in neurological disease. The gene for benign neonatal epilepsy maps to 20q13.2–13.3 and the prion protein gene, involved in neurodegeneration, is located at 20pter-p12. The developmental genes, PAX1 is located at 20p11.2 and bone morphogenetic protein-2 at 20p12.

Chromosome-20 abnormalities including ring formation and deletions have been noted in several disease conditions. Ring formation of chromosome-20 was observed in an infant suffering epileptic seizures, mental retardation and behavioral disturbances[73]. Deletions of the long arm of chromosome-20 have been observed in some patients with myeloid leukemia and myelodysplastic syndromes[78,79], and in patients with small cell lymphocytic lymphoma[77,112]. Interestingly, the region of chromosome-20 containing neuronatin is also the region that is commonly deleted. The abnormalities of chromosome-20 described above occurred postnatally after completion of brain formation, a time when neuronatin mRNA expression is normally repressed. As neuronatin is primarily expressed in the developing brain, it is more likely that the consequences of neuronatin dysfunction will be manifested during embryogenesis rather than after completion of maturation.

The human neuronatin gene is 3973 bases long (SEQ ID No:6; GenBank U31767; FIG. 10) and has three exons and two introns, and is described in detail in the Examples herein below. The gene transcribes two alternatively spliced mRNA isoforms. The α-form contains all three exons and the β-form contains only exons 1 and 3. The middle exon has been spliced out in the β-form, which is the isoform studied in this report. The deduced proteins for human α- and β-form are highly conserved when compared to rat neuronatin cDNA (#U08290 (α-form) and #U09785 (β-form)). The coding regions of both species were identical, except for the substitution of two residues near the C-terminal end of the proteins. This high degree of conservation in mammalian species indicates the functional importance of the neuronatin gene. The 5'-flanking region of neuronatin cap site has a region at about −300 that is highly homologous to neural restrictive silencer element (NRSE). NRSE may govern the neuron-specificity of three other genes, SCG10[95], sodium channel-II[86] and synapsin-I[88]. SCG10 is growth-associated protein of 22kd that is expressed in neuronal derivatives of the neural crest. At E11.5 in the rat, it first becomes expressed in sympatho-adrenal progenitor cells. Thereafter, SCG10 levels are strongly upregulated in sympathetic ganglia and suppressed in adrenal medulla. NRSE is located at about −1500 in the 5'-flanking region of the SCG10 gene. Protein factors, present in non-neuronal cell types, are believed to bind NRSE and silence the transcription of this gene. NRSE elements have also been noted at about −1000 in sodium channel-II, and at about −200 in synapsin-I. Although functional analyses using constructs of the 5'-flanking region of SCG10 and sodium channel-II have shown that deletion of NRSE results in loss of neuron specificity, the evidence in the case of synapsin-I is less certain. However, adjacent to the NRSE element in synapsin-I is the region CGCCCCCGC, a high affinity zif268/egrl binding site[76,109]. zif268/egrl is a zinc finger transcription factor, also known as NGFIA, Krox24 and TIS8, and is an immediate early gene. Based on the degree of homology to the consensus sequence, the NRSE of neuronatin may function to silence expression in non-neuronal tissues. A functioning NRSE in neuronatin would account for the brain (and neuron)-specific expression of this gene.

The above discussion provides a factual basis for the use of neuronatin. The methods used with and the utility of the present invention can be shown by the following non-restrictive examples and figures.

EXAMPLES

GENERAL METHODS:

Fischer 344 Rats: Healthy Fischer 344N/NIA rats, an inbred strain,[10] obtained from the National Institute of Aging, Bethesda, Md. were studied at 3 days (neonate), 3 months (young adult) and 33 months (aged adult) of age. At 3 months of age, the rat is fully mature and at 33 months it is senescent.[59] This is an inbred strain that has been extensively used in aging research. Careful longitudinal studies in large numbers of aging Fischer 344 rats have not revealed significant neoplastic pathology in the brain even at 33 months of age.[9,10] In contrast, nearly all animals at that age exhibit testicular interstitial cell tumor. The central nervous system is entirely normal in Fischer rats less than 18 months of age. Thereafter, about 4–8% of animals exhibit pituitary adenoma, about 1–2% show ischemic changes, and the majority (80%) show well defined nonstaining vacuoles, adjacent to or within neurons. The remarkable absence of neoplastic pathology in the brain makes the Fischer a good source for study of mammalian brain aging and is a preferred model for aging studies with the National Institute of Aging.[10] Studies of stability and sequence complexity of brain mRNA in aging Fischer rats (and Sprague-Dawley) have revealed no major alterations.[11] Except where noted, all animals used were male.

Antibody Production: Antibodies may be either monoclonal or polyclonal. Conveniently, the antibodies may be prepared against a synthetic peptide based on the sequence, or a peptide prepared recombinantly by cloning techniques or the natural gene product and/or portions thereof may be isolated and used as the immunogen.

Such proteins or peptides can be used to produce antibodies by standard antibody production technology well known to those skilled in the art. For a general review see Harlow and Lane, *Antibodies: A Laboratory Manual*, Cold Spring Harbor Laboratory, Cold Spring Harbor, N.Y., 1988. Commercial sources (Bio-Synthesis, Inc. Lewisville, Tex.) were also utilized to prepare antibodies to neuronatin protein.

For producing polyclonal antibodies, a host, such as a rabbit or goat, is immunized with the protein or peptide, generally with an adjuvant and, if necessary, coupled to a carrier; antibodies to the protein are collected from the sera. In a preferred embodiment, NZW rabbits were immunized.[25]

For producing monoclonal antibodies, the technique involves hyperimmunization of an appropriate donor with the protein or peptide fragment, generally a mouse, and isolation of splenic antibody producing cells. These cells are fused to a cell having immortality, such as a myeloma cell, to provide a fused cell hybrid which has immortality and secretes the required antibody. The cells are then cultured, in bulk, and the monoclonal antibodies harvested from the culture media for use.

Based on the hydrophobicity plot generated for the deduced neuronatin protein, 15 amino acids were identified at the C-terminal as being antigenic. This sequence was synthesized (Bio-Synthesis, Lewisville, Tex.) and used for immunization.

General methods in molecular biology: Standard molecular biology techniques known in the art and not specifically described were generally followed as in Sambrook et al., *Molecular Cloning: A Laboratory Manual*, Cold Springs Harbor Laboratory, New York (1989, 1992), and in Ausubel et al., *Current Protocols in Molecular Biology*, John Wiley and Sons, Baltimore, Md. (1989). Polymerase chain reaction (PCR) was carried out generally as in PCR Protocols: *A Guide To Methods And Applications*, Academic Press, San Diego, Calif. (1990). Reactions and manipulations involving nucleic acid techniques, unless stated otherwise, were performed as generally described in Sambrook et al., 1989, *Molecular Cloning: A Laboratory Manual*, Cold Spring Harbor Laboratory Press, and methodology as set forth in U.S. Pat. Nos. 4,666,828; 4,683,202; 4,801,531; 5,192,659 and 5,272,057 and incorporated herein by reference. High stringency hybridization was undertaken at increased temperatures, i.e. hybridization stringency increases as temperature increases and it becomes less likely for hybridization to occur between strands that are nonhomologous.

Differential Display: Animals were decapitated, brain quickly dissected out, immersed in liquid nitrogen, homogenized and total RNA extracted by acid guanidinium thiocyanate-phenol-chloroform method.[7] The methods used were as previously described.[37,42,68] Total RNA (50 $\mu$g) was treated with DNase-I RNase-free (20 u), human placental RNase Inhibitor (80 u), 10 mM Tris HCl, 1.5 mM MgCl$_2$, 50 mM KCl, incubated at 37° C. for 30 minutes, phenol:chloroform extracted and ethanol precipitated. DNase-I treated RNA (2 $\mu$g) was reverse transcribed using 5'-T$_{12}$MG-3' (2.5 $\mu$M) as the 3'-primer (M=mixture of G, A and C), dNTP (20 $\mu$M), MMLV-Superscript-II (300 u) and MMLV buffer (1 x) (Life Technologies, Grand Island, N.Y.): the preparation was incubated at 35° C. for 60 minutes and then at 95° C. for 5 minutes.[42] Thereafter, the reaction was PCR amplified with a degenerate 10-mer sequence (CAGGCCCTTC (Operon Technologies, Alameda, Calif.) in a concentration of 0.5 $\mu$M. Also included in the reaction were $^{35}$S-$\alpha$dATP (1386 Ci/mmol, 0.5 $\mu$M) and Taq DNA polymerase (2.5 u) (Boehringer Mannheim, Indianapolis, Ind.), in a total volume 20 $\mu$l. The preparation was denatured at 94° C. for 5 minutes, and then cycled 40 times. Each cycle consisted of denaturation at 94° C. for 30 seconds, annealing at 40° C. for 2 minutes, and extension at 72° C. for 30 seconds. Thereafter, the samples were extended at 72° C. for an additional 5 minutes, and then held at 4° C. Loading buffer was added and the samples electrophoresed on 6% acrylamide DNA sequencing gels under denaturing conditions. The gel was dried at 80° C. for 45 minutes and exposed to film (X-OMAT-AR, Eastman Kodak, Rochester, N.Y.) overnight at −70° C. cDNA fragments seen to be strongly expressed only in the neonatal brain were cut out of the gel, phenol-chloroform extracted, ethanol precipitated and PCR amplified using the same set of primers and conditions used in the first amplification reaction for differential display. The presence of amplified PCR products was confirmed on 1.5% agarose gels.

Northern Blotting: Initially, partial sequences extracted from the differential display gel were used as probes in Northern blots containing brain RNA from neonatal, young adult and aged rat brain. Once the full length cDNA sequence was determined, this was also used in two sets of Northern blots, one containing rat brain RNA and the second containing human fetal and aged brain. The procedure for the Northern blots was as previously described.[33] Briefly, 15 µg of total RNA containing 0.1 µg/ml of ethidium bromide was electrophoresed on denaturing formamide gels. The amount of RNA applied across the lanes was estimated to be comparable by UV photography. The gel was transferred onto nitrocellulose by overnight capillary transfer. The membrane was cross-linked, baked, and prehybridized in a solution containing 1% bovine serum albumin, 7% SDS, 0.5 M sodium phosphate pH 7.0 and 1 mM EDTA for 2 hours. Hybridization was continued overnight in the presence of $1\times10^6$ cpm/ml of random prime labelled probe, at 65° C. The membrane was washed (1% SDS, 40 mM $Na_3PO_4$ pH 7.0, 1 mM EDTA) at room temperature for 30 minutes, and then twice at 65° C. for 30 minutes. The washed membrane was autoradiographed for about 6 hours.

Cloning and sequencing CDNA Fragments: cDNA fragment isolated from differential display gel were cloned into pCR™ (Invitrogen, San Diego, Calif.) as described.[8] The cloned vector was used to transform TA One Shot™ competent cells. White colonies were selected for plasmid preparation from plates containing Kanamycin and Bluo-gal (Life Technologies, Grand Island, N.Y.). The inserts were amplified using primers across the cloning site.

The reaction included the plasmid template (1 µg), T7 primer (0.4 µM), SP6 primer (0.4 µM), dNTP (100 µM), buffer (1 x) and Taq polymerase (2.5 u). The reactions: were denatured at 94° C. for 5 minutes. Thereafter, samples were amplified for 35 cycles. Each cycle consisted of denaturation at 94° C. for 1 minute, annealing at 62° C. for 2 minutes and extension at 72° C. for 3 minutes. This was followed by extension at 72° C. for 5 minutes, and samples held at 4° C.

25 µl of the sample was loaded on 1.5% agarose gel containing 0.1 µg/ml ethidium bromide, electrophoresed using Tris-acetate buffer (1 x), and photographed using UV light. A 100 bp DNA ladder (Life Technologies, Grand Island, N.Y.) was run simultaneously as a control.

Double stranded sequencing of the cloned cDNA insert was carried out using Sequenase Version 2.0 (United states Biochemicals, Cleveland, Ohio). Five µg of template was denatured, annealed with T7 or SP6 primers, labelled with $^{35}$S-dATP and extended by the chain termination method of Sanger.[58] The presence of the anchored 3'-primer was used to locate the cloned insert.

Sequencing of Full-Length CDNA: Sequencing was carried out using cycle sequencing with the fmol™ Sequencing System (Promega, Madison, Wis.). Sequencing was carried out in both directions using custom made primers (DNA International, Lake Oswego, Oreg.) as follows:

F1. 5'-CTT-CTT-CCT-TTC-CTT-CTC-ATC-TCA-GC-3' (SEQ ID No:7)
R1. 5'-CTC-CTG-TGC-TTC-TCG-ACC-AGC-ATG-3' (SEQ ID No:8)
F2. 5'-GTG-GGT-GCA-GGA-GCT-CAT-TC-3' (SEQ ID No:9)
R2. 5'-CAG-CGA-CAG-ATC-TAC-ATG-AG-3' (SEQ ID No:10)
9F1. 5'-GAC-CAG-GGA-TAA-GCA-AGA-TCA-G-3' (SEQ ID No:11)
9R1. 5'-GCG-AGA-ACT-CTT-CAG-GTA-CT-3' (SEQ ID No:12)
9F2. 5'-CCC-ACT-AGT-TTT-CTT-AAC-CC-3' (SEQ ID No:13)
9F3. 5'-ATT-CTG-CTG-GTT-GGT-GGG-GG-3' (SEQ ID No:14,)
9R1R. 5'-CTG-GGT-AGG-ATT-CGC-TTT-3' (SEQ ID No:15)
9R2. 5'-CAG-GTG-CTC-CTG-TGC-TTC-3' (SEQ ID No:16)
9F4. 5'-CTG-GGA-AAG-GAA-CTG-ATG-3' (SEQ ID No:17)
3R1. 5'-TCG-GCT-GGT-ACA-TCT-TCC-GCG-3' (SEQ ID No:113)

Determination of Protein Expression in Cytosolic and Membrane Fractions: Six neonatal pups (3 days) and one adult rat brain were used. Animals were decapitated, brain removed, washed with TEN (10 mM Tris-HCl pH 7.4, 1 mM EDTA, 0.1 M NaCl), cut into small pieces, placed in 10% sucrose in a buffer containing 50 mM Tris-HCl pH 7.4, 2 mM EDTA, 0.1 mM PMSF, 1 mM DTT, 1 µg/ml Leupeptin, homogenized, filtered through four layers of cheese cloth and centrifuged (27,000×g for 30 minutes). The supernatant (cytosolic fraction) was saved. The pellet fraction was resuspended in 10% sucrose buffer and applied to a 30%–56% sucrose gradient and centrifuged at 27,000×g for two hours. The membrane fraction was collected from the interface of the 10% and 30% sucrose. Protein in the cytosolic and membranal fractions were quantitated, and 50 µg of protein applied to each lane of a 5%–20% acrylamide gradient SDS gel and stained with coomassie blue. A low molecular weight standard marker was also electrophoresed simultaneously.

Preparation of Constructs Containing Neuronatin: Sense and nonsense constructs of neuronatin are transferred into NIH3T3 cells using PLXSN (Dr. A. Dusty Miller, Seattle, Wash.), a replication-defective retroviral vector. The order of genetic elements in this vector are: long terminal repeat (LTR); cloning sites for EcoRI, HpaI, XhoI and BamHI; simian virus 40 early promoter and neo. Neuronatin, will be transfected using retroviral constructs containing neuronatin-α coding region in the sense and nonsense orientations.[48] Based on the restriction map of neuronatin cDNA, digestion with EcoRI and XhoI released a 556bp 5'-terminal fragment containing the coding region which is extracted and cloned into the vector following predigestion of the vector with EcoRI and XhoI ("Sense construct"). In a separate reaction, digestion of neuronatin cDNA was also carried out with EcoRI and XhoI and the 639bp 3'-terminal fragment extracted and cloned into the vector which had been digested with EcoRI and XhoI ("nonsense construct").

High titer virus production will be carried out by transient transfection, using the calcium chloride method, of two packaging cell lines, first PE501 and then PA317. The virus-containing medium is used to infect NIH3T3 cells and selection carried out using cloning cylinders in the presence of G418 (0.75 mg/ml). In order to confirm transfer of neuronatin into NIH3T3 cells, the transfected cells obtained after G418 selection are pooled, grown in mass culture and used to isolate RNA for Northern blotting. In an alternative embodiment, sense and nonsense constructs can be transferred into LaNI a neuronally derived cell line.

EXAMPLE 1

Cloning and Sequencing of the rat cDNA Fragment cDNA fragments isolated from a differential display gel were cloned[8] and used to transform TA One Shot™ competent cells. White colonies were selected for plasmid preparation from plates containing Kanamycin and Bluo-gal (Life Technologies, Grand Island, N.Y.). The inserts were amplified using primers across the cloning site. In the absence of an insert, the predicted size of the amplified product was 188bp. The clone containing the insert exhibited a larger sized product estimated to be about 300bp using a 100bp DNA ladder (Life Technologies, Grand Island, N.Y.) that was run simultaneously. Double stranded sequencing of the cloned cDNA insert was carried out using Sequenase Version 2.0 (United states Biochemicals, Cleveland, Ohio). The partial sequences of five of these fragments, SEQ ID Nos:19–23, were unique with no homology in GenBank.[3] These sequences were used to isolate the full length sequence from the rat brain cDNA library applicants constructed.

EXAMPLE 2

Construction of Fischer Rat Brain CDNA Library

A cDNA library was prepared using a mixture of RNA from neonatal, young adult and aged Fischer 344 rat brain. The overall scheme was as previously described[32] and as generally further described in Sambrook et al., *Molecular Cloning: A Laboratory Manual*, Cold Springs Harbor, N.Y., 1989.

High quality total RNA (1 mg) was separated by the single step acid guanidinium thiocyanate-phenol-chloroform method.[7] Through all the steps of the library construction, products were monitored by UV spectrophotometry, DNA dipstick (Invitrogen, San Diego, Calif.), or by $^{32}$P-dCTP incorporation.

Total brain RNA was treated with RNase-free DNase-I (1 u/32 μg of RNA) in order to digest contaminating genomic DNA. DNase-free RNA was applied to oligo-dT cellulose column (Pharmacia, Piscataway, N.J.). mRNA, eluted by 0.5 M NaCl in 1×TE (10 mM Tris HCl, 1 mM EDTA), represented 2.7% of the total RNA pool. 4μg of mRNA was used to synthesize cDNA using 200 u of Superscript-II MMLV reverse transcriptase, 0.5 μg of oligo-dT$_{12-18}$, in 80 μl of 50 mM Tris, pH 8.3 buffer. All steps up to this stage used dH$_2$O treated with 0.02% DEPC and autoclaved, and contained 2 u/μl of RNase inhibitor.

The resulting RNA-DNA hybrids were converted to ds-cDNA in 100 μl of 20 mM Tris pH 7.5, 4 u of RNase-H and 46 u of DNA polymerase. ds-cDNA was blunt ended using mung bean nuclease (43 u/200 μl of reaction mixture), 30 mM sodium acetate pH 5.2 and 1 mM Zn$^{2+}$as an activator. For high efficiency cloning of blunt ended ds-CDNA, EcoRI adapters with a nested NotI site (Life Technologies, Grand Island, N.Y.) were ligated to the ends using 20 u of T4 Ligase, 66 mM Tris pH 7.5, in a 50 μl reaction volume. NotI recognizes an 8-base site which rarely exists in ds-cDNA (about one site per 65 kb) increasing the chances of excising the intact insert after cloning. The excess adapters and smaller cDNA fragments (<500 bp) were removed by cDNA fractionation column (Life Technologies). ds-cDNA with ligated EcoRI(NotI)-adapters were cloned into the single EcoRI site located at the 3'-end of LacZ gene in λgt11.

To minimize background, the dephosphorylated λgt11 EcoRI arms (Life Technologies) were ligated with phosphorylated EcoRI(NotI)-adapter-ds-cDNA. Phosphorylation of EcoRI(NotI)-adapter-ds-cDNA was carried out with 40 u of T4 nucleotide kinase, 66 mM Tris pH 7.5, 1 mM ATP, in 250 μl reaction volume. Finally, the recombinant λgt11 phage were packaged in vitro using λ Packaging System (Life Technologies), and used to infect *E. coli* Y1090(R$^-$M$^-$ ΔLacU169). The efficiency was about 3.5×10$^5$ pfu/μg cDNA. More than 90% of the plaques were detected by blue/white selection to contain recombinant phage.

EXAMPLE 3

Screening of Library for Rat Neuronatin

Using the unique partial rat cDNA fragment, applicant screened about 25,000 plaques. The probe was labelled with $^{32}$P-dCTP by the random primer method (Boehringer Mannheim, Indianapolis, Ind.) to about 10$^8$–10$^9$ cpm/μg DNA. Nine plaques showed strong hybridization (at 73° C.). These nine plaques were purified, DNA prepared and digested in separate reactions with EcoRI and NotI. Both these restriction enzymes released single fragments suggesting the absence of these restriction sites within the insert. One plaque released an insert of about 1.2–1.3 kb, corresponding to the size of the mRNA species detected in the Northern blot using the partial cDNA sequence. This clone was fully sequenced (SEQ ID No:1).

EXAMPLE 4

Restriction Enzyme Mapping

A restriction map (FIG. 3) of the cDNA sequence was generated[3] using six restriction enzymes: EcoRI, NotI, PstI, BamHI, NcoI and XhoI. The predicted fragments that were generated are listed in Table 3. There were no sites for EcoRI and NotI.

TABLE 3

| | ENZYME | SITES | PRODUCTS (bp) |
|---|---|---|---|
| 1. | EcoRI | None | 1195 |
| 2. | NotI | None | 1195 |
| 3. | PstI | 112,214,1160 | 35,102,112,946 |
| 4. | NcoI | 40,511,633 | 40,122,471,562 |
| 5. | BamHI | 925 | 270,925 |
| 6. | XhoI | 556 | 556,639 |

EXAMPLE 5

Neuronatin is differentially expressed in the neonatal brain.

The full length cDNA sequence (SEQ ID No:1), designated neuronatin (neuronatin-α), was used in Northern blotting to confirm selective expression in neonatal brain (FIG. 4).

When used as a probe to study tissue expression, neuronatin was expressed only in the brain and not in the heart, kidneys or liver of neonatal rats as shown in FIG. 5. Total RNA (20 μg)[7], was electrophoresed in a denaturing formamide gel. The gel was stained with ethidium bromide, photographed under UV (bottom panel), and transferred to a nylon membrane by overnight capillary transfer. The membrane was cross linked, baked and hybridized overnight with 1×10$^6$ cpm/ml of $^{32}$p-labeled neuronatin-α at 65° C., washed at 65° C., and autoradiographed for about 6 hours (top panel). The blot was then stripped and rehybridized with human glyceraldehyde-3 phosphate dehydrogenase (G3PDH) (middle panel).

Rapid brain growth due to a surge in neuronal proliferation and migration is a characteristic feature of the later stages of mammalian fetal development. Following the closure of the neural tube, waves of neuroblasts originating in the neuroepithelium of the ventricular zone migrate into the surrounding marginal zone. Although neuronal proliferation begins at embryonic day 12–13 (E12–13) in the rat, the process accelerates later in development and continues into the neonatal period accounting for much of the subsequent gain in brain weight. Therefore, the time sequence of neuronatin mRNA expression was studied during different stages of gestation and post-natal development in both male and female rats.

Figure 6:
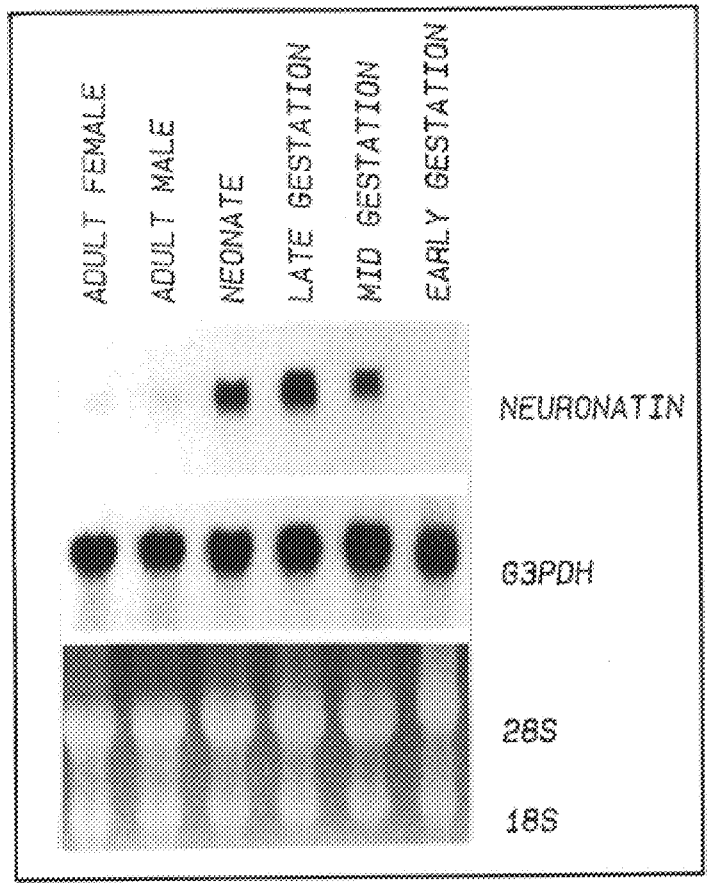
FIG. 6 is a photograph of Northern hybridization gels studying changes in neuronatin mRNA expression during rat development, E7–10 (early gestation), E10–14 (mid-gestation), E16–19 (late-gestation), neonate (3 days), adult (3 months) male and female rats and hybridized as in FIG. 5.

Northern blotting was carried out using RNA extracted from rat fetuses at E7–10 (early gestation), E10–14 (mid-gestation), E16–19 (late-gestation), and, in the neonate (3 days), adult (3 months) male and female rats. Neuronatin mRNA was not expressed in the early embryonic period. It first appeared in mid embryonic stages of development and its expression peaked later at E16–19, the time in development when there is a marked increase in brain weight due to rapid neuronal proliferation and migration. Postnatally, the expression of neuronatin declined such that only minimal levels were present in adulthood. Neuronatin mRNA first appeared at E10–14, peaked at E16–19 then declined after birth (FIG. 6).

Figure 7:
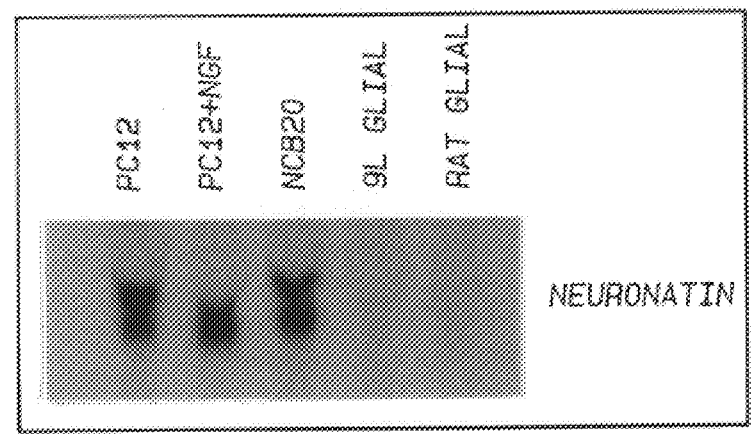
FIG. 7 is a photograph of Northern blots screening neuronal and glial cell lines: PC12 (rat pheochromocytoma), nerve growth factor (NGF) treated PC12 cells, NCB20 (rat neuroblastoma×Chinese hamster cortical neurons), 9L (rat glial cell line), and a primary rat glial cell line.

In order to determine the cell type in which neuronatin was expressed, neuronal and glial cell lines were screened. Neuronatin was expressed in PC12 (rat: pheochromocytoma) (ATCC, Bethesda, Md.) and NCB20 (rat: neuroblastoma×Chinese hamster cortical neurons) (M. Nirenberg, Bethesda, Md.) cells, both neuronal-type cell lines; but not in the rat glial cell lines, 9L and a primary glial line (S. Gautam, Detroit, Mich.) (FIG. 7). Therefore, neuronatin is selectively expressed during late fetal and early neonatal brain development and the mRNA is neuron-specific.

The deduced neuronatin protein had a size of 9.2kD with a highly hydrophobic N-terminal arranged in an α-helix,[28] and a hydrophilic C-terminal suggesting that it is membrane-bound.

EXAMPLE 6

Alternatively Spliced Forms of Neuronatin

Total RNA was extracted from the brain of neonatal (3 days), young adult (3 months) and aged adult (33 months) rats, reverse transcribed into cDNA and differentially displayed on denaturing sequencing gels,[37,42,68] as discussed herein above. A total of 35 cDNA bands which were selectively expressed in one or other age group were extracted from the gel, PCR amplified, and used as probes for Northern blotting.[7,33] However, only seven of these cDNA bands were confirmed on Northern blotting to be selectively expressed. These fragments were TA-cloned into pCR™ (Invitrogen, San Diego, Calif.)[8] and sequenced across the insert site with T7 and SP6 primers using Sequenase Version 2.0 (United States Biochemicals, Cleveland, Ohio).[58] When compared in the GenBank database,[3] three of the seven cDNA fragments had novel sequences that were expressed in the neonatal brain. These three unique but partial cDNA sequences were used to probe a λgt11 rat brain cDNA library (EXAMPLE 2).

One cDNA fragment hybridized nine clones; of these, four were between 1.2 and 1.3 kbp, one about 2 kbp, and the remaining four were 0.5–0.8 kbp. The clones in the 1.2–1.3 kbp range corresponded in size to the mRNA species detected. These four clones were sequenced using the fMol™ Sequencing System (Promega, Madison, Wis.) in both directions with custom made primers (SEQ ID Nos:7–18; DNA International, Lake Oswego, Oreg.). All four clones had identical 5'- and 3'-untranslated regions, and the same type and location of translation initiation (GAACCATGG),[38] stop (TGA) and termination (AATAAA) signals.[65]

Two of these four clones were identical including having a coding region of 162 nt, designated β, similarly, the remaining two clones were also identical with each other with a coding region of 243 nt, designated α. The two alternatively spliced forms of the gene, neuronatin (nnn), were expressed in developing mammalian brain. The two forms, α and β, had the same open reading frame and were identical except that neuronatin-α had three exons and neuronatin-β two exons. The cDNA sequences for the longer, neuronatin-α (SEQ ID No:1), and shorter, neuronatin-β (SEQ ID No:2) (FIG. 9), species were confirmed by sequencing two separate clones for each spliced form of neuronatin (nnn).

Figure 9:
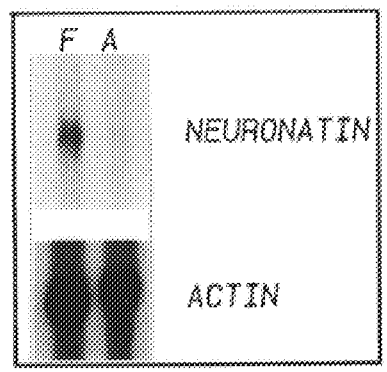
FIG. 9 is a photograph of Northern blots of human fetal (F) (18–24 weeks old) and human aged (A) brain (60 years old) hybridized with full length cDNA sequence for neuronatin-α.

The two forms of neuronatin mRNA and their deduced protein sequence for neuronatin-α (SEQ ID No:3) and neuronatin-β (SEQ ID No:4) were novel based on analysis in GenBank. The restriction maps generated were confirmed using six enzymes, EcoRI, NotI, NcoI, BamHI, PstI and XhoI. The difference between the neuronatins was confined to a portion of the coding region. Neuronatin-α has an additional 81 bp sequence inserted into the coding region (FIG. 9). Surprisingly, this additional stretch of cDNA had the prototypical features of an intron,[41] including the consensus sequences GT at the 5'-end, AG at the 3'-end, and the branch site, TCGAAAT, located 33 nt upstream of the 3'-end. Although exhibiting characteristics of an intron and absent in neuronatin-β, this segment functioned as the middle exon of neuronatin-β.

The cDNA for neuronatin-a has three exons, the first exon was from position 1 to 72 (72 nt, 24 aa); the third exon from position 73 to 162 (90 nt, 30 aa); and the second exon is inserted between positions 72 and 73 and consists of the 81 bp sequence coding for 27 amino acids as shown in the box in FIG. 8. Although the CDNA for neuronatin-β does not have the middle exon, it maintained the same open reading frame as that in neuronatin-α suggesting that the two forms are alternatively spliced.

Northern hybridization revealed that both forms of neuronatin CDNA hybridized to an mRNA species of about 1.2 kb. Therefore, unless otherwise noted, studies in this application were carried out using neuronatin-α (SEQ ID No:1).

EXAMPLE 7

Human Neuronatin
Screening of Human Fetal Brain cDNA Library & Isolation of Human Neuronatin cDNA The human fetal brain cDNA library was a random primed 5'-stretch plus λgt 11library prepared using oligo-(dT) (Clontech, Palo Alto, Calif.). RNA for preparing the library was obtained from tissue pooled from seven spontaneously aborted human fetuses of 20–26 weeks gestation (Clontech, personal communication). A titer of 1.6×10$^8$ pfu/ml was used for screening. E. coli Y1090r⁻strain (BRL, Gaithersburg, Md.) was transfected in liquid lysate and an estimated 20,000 plaques prepared. The infection was carried out at 37° C. for 30 min in 40 ml of phage dilution buffer (50 mM Tris, 90 mM NaCl, 0.01% gelatin, pH 7.0) to a cell density of 0.3 at 600 nm. The host cells used for infection were pre-induced by treatment with 0.2% maltose overnight in LB supplemented with 10 mM $MgSO_4$. The infected cells were mixed with 10 times its volume of LB containing 0.7% agar (pre-warmed to 49° C.) and divided (5 ml/dish) into 80 dishes (100 mm each). All dishes were pre-loaded with 2% agar in LB medium. After overnight incubation at 37° C., the plaques measuring about 1–2 mm (250–300 plaques/dish), were transferred onto nitrocellulose (Gelman, Ann Arbor, Mich.). The membranes were denatured in a solution containing 0.5 M NaOH and 1 M NaCl, neutralized using buffer (0.7 M phosphate, pH 6.5), each applied for 2 min, and quickly rinsed in 10×SSC. The membranes were cross-linked using short wave UV for 5 min and used for Southern hybridization. The rat neuronatin cDNA probe (20) was $^{32}$P-labeled by random priming (Promega, Madison, Wis.) and purified using column separation (Pharmacia, Upsala, Sweden). The hybridization was performed overnight at 65°–70° C. with $0.5–1×10^6$ cpm/ml of probe at a specific activity of $0.5×10^9$ cpm/µg in 250 ml of a hybridization solution containing 5×SSC (70 mM sodium citrate, 750 mM NaCl, pH 7.0), 1×Denhart's solution (0.02% ficoll, 0.02% polyvinylpyrrolidone, 0.02% BSA), 0.5% SDS and 200 µg/ml salmon sperm DNA. The blots were washed three times in 0.2×SSC containing 0.1% SDS for 10 min and autoradiographed overnight between intensifying screens.

Plaques showing strong hybridization were screened again and purified. The purified phage was used to re-infect *E. coli* Y1090r⁻cells, and a 300 ml lysate prepared (Sambrook et al, 1989). The lysate was treated with RNase A (100 µg/ml) and DNase I (10 U/ml) for 2 hrs at 37° C. The phage was precipitated using 12.5% PEG 8000 and 7 M NaCl, incubated at 0° C. for 1 hr, and centrifuged (15,000×g for 30 min). Phage DNA was isolated by phenol/chloroform extraction and ethanol precipitation. Human cDNA inserts were released by digestion of phage DNA with EcoRI, and subcloned into pGEM7fZ(+) vector at the same restriction site to generate constructs in the forward and reverse orientations[80].

Fifty µg of closed circular plasmid DNA prepared by the acid method was completely digested with a combination of SacI and HindIII[115]. The vector with intact SP6 promoter on the SacI side would be protected, while the human cDNA fragment on the HindIII side was accessible to digestion by ExoIII in a 5'-direction. A series of deletion constructs were generated by incubation with ExoIII[3,84]. The concentration of ExoIII used was 10 U/µg DNA. Aliquots of the reaction mixture kept at 22° C. were removed at 1.5 min intervals and placed at 0° C. The cohesive end was blunt-ended by incubation with S1 nuclease (12 U/µg DNA) at 22° C. for 30 min, and filled-in using Klenow (2 U/µg DNA) at 37° C. for 5 min. The deleted DNA fragments were ligated using $T_4$ DNA ligase and transformed into *E. coli* JM109 strain. The plasmids were selected as described[91.]

DNA sequencing was carried out using the dideoxy-sequencing[45] and thermal cycle amplification with the fMol Sequencing System (Promega, Madison, Wis.). The SP6 primer was used to sequence the ExoIII constructs, and custom synthesized oligonucleotides (DNA International, Oswego, Oreg.) were used to confirm the open reading frame.

Northern Hybridization

Total RNA from human fetal (18–24 weeks) and adult (60 yrs) brain was also obtained from Clontech, Palo Alto, Calif. RNA from rat tissues was isolated by the acid guanidinium thiocyanate method[7]. Briefly, fresh tissue samples were homogenized on ice in 25 mM sodium citrate buffer (pH 7.0) containing 4 M guanidinium thiocyanate, 0.5% sarcosyl and 100 mM β-mercaptoethanol. Protein and DNA were eliminated by mixing with 100 mM sodium acetate, 0.5×volume of phenol and 0.1×volume of chloroform, followed by centrifugation. The RNA was precipitated with an equal volume of isopropanol and washed with 75% ethanol. The RNA pellet was dissolved in DEPC-$H_2O$ and kept at −80° C.

Samples of total human RNA (15 µg) were mixed with 3×volume of denaturing and staining solutions (25 mM MOPS, 20% formaldehyde, 50% formamide, 100 ng/ml ethidium bromide and 2 mM EDTA). The mixture was incubated at 65° C. for 5 min, combined with 0.25 volume of loading buffer (50% glycerol, 0.1% bromophenol blue and 2 mM EDTA), and applied on 10% formaldehyde-1.5% agarose gel and electrophoresed. RNA was transferred onto nylon membrane (Micro Separations, Westboro, Mass.), and UV cross-linked for 3 min. The blot was prehybridized in a solution containing 5×SSPE (40 mM $NaH_2PO_4$, 750 mM NaCl, 4 mM EDTA, pH 7.4), 10×Denhardt's solution, 50% formamide, 2% SDS and 100 µg/ml denatured salmon sperm DNA at 42° C. for 3 hrs. Hybridization was continued with a fresh batch of the same solution containing $^{32}$P-labeled human neuronatin cDNA in a concentration of $5–10×10^6$ cpm/ml, at a specificity of $1–2–10^9$ cpm/µg DNA. The hybridization was performed at the same temperature for 18 hrs. The blot was washed three times using 2×SSC/0.05% SDS at room temperature for 10 min and autoradiographed.

Hydropathy and Densitometry Analyses

The protein structure was analyzed using the program of Hitachi Hibio Prosis Protein Analysis System. The window size was set at 7. KYTE.THR mode was selected for calculation (25). Quantitation of northern blots was carried out using Bio-Rad GS-670 Imaging Densitometer and Molecular Analysis System. Quantitation of changes in neuronatin mRNA expression was controlled with glyceraldehyde 3-phosphate dehydrogenase (G3PDH) mRNA expression using Microsoft Excel software.

Screening of Somatic Hybrid Cell Panel

Human-rodent somatic cell hybrid panel (Bios, New Haven, Conn.) was screened using primers designed to specifically hybridize the 3'-untranslated region of human neuronatin cDNA. The two primers, N-75 (5'-TGCGCCTCTACTGCACCGC-3') and N-94 (5'-CCCTGGTCTCATGCAGTTGTGG-3') flanking the poly-A signal site were synthesized to amplify a 193 bp product that would be expected to be specific for human neuronatin gene. The PCR reactions were carried out with hot-start and by a two step amplification protocol. Template DNA (190 ng) was used for the first step in a volume of 50 µl containing 50 mM Tris (pH 8.3), 80 mM KCl, 2.5 mM $MgCl_2$, 195 µM dNTP, 40 ng each of primers N- 75 and N-94, and 0.5 U of Taq polymerase. Each cycle consisted of denaturation at 95° C. for 1 min, annealing at 45° C. for 30 secs, and extension at 72° C. for 2 min, for a total of 30 cycles. A 5 µl aliquot from the resulting reaction mixture was taken through a second amplification step with 1 U Taq polymerase for 25 cycles, each cycle consisting of denaturation, annealing and extension at 95° C., 56° C. and 72° C. respectively, for 1 min each. The amplified fragments were separated on 1.5% agarose gel and visualized after staining with ethidium bromide.

Fluorescence In Situ Hybridization

Fluorescence in situ hybridization (FISH) was carried out using biotin-labeled human neuronatin genomic clone as the probe and human lymphocyte metaphase spreads. Metaphase cells were obtained from phytohemagglutinin-stimulated human lymphocyte cultures using established cytogenetic procedures[110]. Human neuronatin genomic clone was biotin-labeled by nick-translation using a combination of DNA polymerase I and DNase I (Clontech, Palo Alto, Calif.). The labeling reaction containing 1 μg of chromatographically purified lambda phage DNA, 10 units of polymerase I and 400 pg of DNase I, was incubated at 16° C. for 3 hrs in a 100 μl reaction. The mixture also contained 20 mM biotin-21-dUTP, 20 μM each of DATP, dCTP and dGTP, 8 mM β-mercaptoethanol, 10 μg/ml BSA and 50 mM Tris buffer (pH 7.5). The reaction was stopped by adding 20 mM EDTA. The labeled probe was purified by Sephadex G-50 (Nick Spin Columns, Pharmacia, Alameda, Calif.). Before hybridization, chromosomes were characterized by G-banding using a modified protocol.[75,103] Briefly, the slides were treated with 100 μg/ml RNasie A in 2×SSC at 37° C. for 1 hr and dehydrated in 70%, 95% and 100% ethanol at room temperature for 2 min each, and allowed to air dry. The slides were incubated at 70° C. for 2 min in a denaturing solution containing 2×SSC and 70% formamide, dehydrated at 0° C. in the same ethanol series. The biotin-labeled probe (100–150 ng) and 50 μl of hybridization buffer (Oncor, Gaithersburg, Md.) were denatured at 70° C. for 5 min. The denatured probe was applied to the denatured slide, cover-slipped, sealed with rubber cement and incubated overnight at 37° C. Following hybridization, the slides were washed with 50% formamide in 2×SSC for 15 min and in 2×SSC at 37° C. for 8 min. The hybridization signal was detected and amplified using Texas Red/avidin and anti-avidin antibody (Oncor). The chromosomes were counter-stained with 4', 6-diamidino-2-phenylindole. In a parallel experiment, signal was amplified using FITC-avidin and anti-avidin antibody. The chromosomes were counterstained with propidium iodide.

Results
Isolation and Sequencing of Human Neuronatin cDNA

Using rat neuronatin probe to screen the human fetal brain cDNA library, five plaques showing strong hybridization were identified. The sizes of the inserts in these five plaques were analyzed by PCR using the λ-forward and reverse primers flanking the cloning site. Two plaques, containing the longest inserts of about 1.2 kb, were purified. Both ends of the inserts were sequenced. Although, this revealed that both cDNA clones were generated from the same mRNA, one possessed the complete 3'-end with poly(A) signal but the other did not. The EcoRI digestion and PCR results indicated that both inserts contained no internal EcoRI sites. Therefore, the inserts were released intact by digestion with EcoRI, sub-cloned into pGEM7fZ(+) at the same restriction site, and used for sequencing. The resulting plasmids, pDR101 and pDR102, carried the same human cDNA inserts but in opposite orientations. These two plasmids allowed applicants to sequence the insert from both ends of the cDNA. Both these clones were used to prepare deletion constructs with a combination of SacI/HindIII and ExoIII digestion. The deletion constructs were ligated, transformed, DNA prepared, and sequenced using SP6 primer and cycle-sequencing. The DNA sequence revealed an open reading frame extending from position 72 bp to 234 bp (GenBank #U25034). Besides this, neuronatin also had an alternatively spliced form which encoded 81 amino acids (GenBank #U25033). Both forms had the same open reading frame. The longer isoform (α) was encoded by all three exons, whereas, the shorter (β) isoform was encoded only by exons 1 and 3. The only difference between the two forms was that the middle exon was spliced out in the β-form. The isoforms possessed a ionsensus translational initiation site[38], GAACCATGG, and a canonical poly(A) adenylation signal, AATAAA, located between 1094 and 1100 bp. GenBank analysis using the BLAST server revealed that neuronatin cDNA had partial homology to the 3'-untranslated region of one form of rat calbindin-D28K isolated by Lomri, et al[44]. There was no homology to any of the other forms of calbindin-D28K present in the database. Moreover, the coding regions of calbindin-D28K and neuronatin were separated by 746 bp. Therefore, neuronatin and calbindin-D28K are two different genes.

Neuronatin Protein Structure and Homology

The deduced gene products for neuronatin α and β were 9.2 and 6.15 kDa respectively. The hydrophobicity plot of human neuronatin CDNA indicated the presence of two distinct domains, a hydrophobic domain at the N-terminal (encoded by exon-1) and a hydrophilic domain at the C-terminal (encoded by exon-3). The middle exon, present only in the α-form was neither hydrophobic nor hydrophilic. The hydrophobic domain contained about 23 amino acid residues. This was a suitable size to form a transmembrane α-helix structure.[70,108] The experimental results also support that it was a membrane protein. When neuronatin cDNA was fused to LacZ, the expressed fusion protein was observed to be anchored in the $E.\ coli$ cytoplasmic membrane. The C-terminal domain of neuronatin was hydrophilic and highly basic, and was 20% (6 of 30 amino acids) constituted by arginine residues. The primary amino acid sequence of human neuronatin showed about 50% homology with two known proteins, PMP1[98] and phospholamban[107], that function as subunits of $H^+$-ATPase and $Ca^{2+}$-ATPase, respectively. The structural organization of these three polypeptides were also similar, each consisting of two domains, a hydrophobic transmembrane domain and a charged hydrophilic domain.

Neuronatin mRNA Expression in Human Fetal Brain

Human neuronatin expression was analyzed by northern hybridization using full length human neuronatin cDNA. As both isoforms were identical, except for the presence of the middle exon in the α-form, applicant used neuronatin-β cDNA as the probe in all northern blotting experiments described in this report. The expression pattern seen was similar to that observed earlier in the rat using neuronatin-α cDNA as the probe.[85] After hybridization with neuronatin, the blot was stripped and rehybridized with human G3PDH as the control probe. Neuronatin mRNA is selectively expressed in human fetal brain (18–24 weeks), compared to the adult (60 yrs) brain. Densitometric quantitation, controlled with G3PDH mRNA, indicated that the expression of neuronatin mRNA in fetal brain was 23 times greater than that in the adult.

Neuronatin mRNA Expression in Other Human Fetal Tissues

A mRNA blot prepared from human fetal (18–24 weeks) brain, lung, liver and kidney (Clontech, Palo Alto, Calif.) was hybridized with human neuronatin CDNA. Neuronatin mRNA was selectively expressed in brain, and not in lung, liver or kidney. Densitometric analysis revealed that the expression in fetal brain was 28, 46 and 138 times higher than in the lung, kidney and liver, respectively. In additional experiments using rat tissue, applicants noted that neuronatin mRNA was not expressed in the heart, skin and muscle.

Neuronatin mRNA Expression During Mammalian Development

In order to investigate the expression of neuronatin mRNA during development, northern analysis was carried out using RNA extracted from rats aged, E7–10, E11–14, E16–19, P3, P90 (3 months) and P990 (33 months) and human neuronatin cDNA as the probe. Neuronatin mRNA first appeared at E11–14, peaked at E16–19, and declined to traces in the adult brain. Quantitation was carried out using densitometry, the level of expression at E7–10 was set as 1 unit. Relative to this, the expression at E11–14 was 8 units, and at E16–19, 44 units. This increase in neuronatin mRNA expression coincided with a rapid increase in brain growth. Postnatally, neuronatin mRNA expression decreased to 9 units by P3 and was at baseline by 3 months of age. The developmental changes seen in the rat are somewhat comparable to the changes seen in the human. Neuronatin mRNA expression in human fetal brain at 18–24 weeks, and that in the rat at about a comparable developmental stage (E11–19), indicated that in both species there was a 20–30 fold increased expression during embryogenesis over that seen in the adult.

not amplify the specific fragment indicating that neuronatin was not located on the end of the long arm. With the deletion construct OF21–2, containing the 20q11.2–20q13 region, amplification of the neuronatin-specific product was observed. The predicted product was also seen with GM10478, which contained chromosome-20 in its entirety. These results indicate that neuronatin gene is located between 20q11.2 and 20q12.1.

TABLE 4

Localization of Neuronatin Gene to Human Chromosome by Somatic Cell Hybrid Discordance Analysis

| Hybrid clone | Neuronatin[a] | Human Chromosome[b] | | | | | | | | | | | | | | | | | | | | | | |
|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Y |
| BIOS010 | − | − | − | − | − | − | − | − | − | − | − | + | − | − | − | − | − | − | − | − | − | − | − | − | − |
| BIOS016 | − | − | − | − | − | − | − | − | − | − | − | − | − | − | − | − | + | − | − | − | − | − | − | − | − |
| BIOS212 | − | − | − | − | − | + | − | − | − | − | − | − | − | − | − | − | − | − | − | − | − | − | + | − | − |
| BIOS324 | − | − | − | − | − | − | − | − | − | − | − | − | − | − | − | − | − | − | + | − | − | − | − | − | − |
| BIOS423 | − | − | − | + | − | − | − | − | − | − | − | − | − | − | − | − | − | − | − | − | − | − | − | − | − |
| BIOS683 | − | + | − | − | − | + | − | − | − | − | − | + | − | + | − | − | − | − | + | − | + | + | − | − | − |
| BIOS734 | − | − | − | − | − | + | − | − | + | − | − | − | − | − | − | − | − | − | − | − | − | − | − | − | − |
| BIOS750 | − | − | − | − | − | + | − | − | − | − | − | − | − | + | + | + | − | − | + | − | − | − | − | − | − |
| BIOS756 | + | − | − | − | − | + | + | + | − | − | − | + | + | + | − | − | − | − | + | + | + | − | − | − | − |
| BIOS803 | − | − | − | − | − | + | − | − | + | − | − | − | − | − | − | − | − | − | − | − | + | + | − | − | − |
| BIOS811 | − | − | − | − | − | − | − | − | + | − | − | − | − | − | − | − | + | + | − | − | − | − | − | − | − |
| BIOS852 | − | − | + | − | − | − | − | − | − | − | − | − | − | − | − | − | − | − | − | − | − | − | − | − | − |
| BIOS867 | − | + | − | − | − | + | − | − | − | − | − | − | + | + | − | − | + | + | − | − | − | − | − | − | − |
| BIOS909 | − | − | − | − | − | + | + | − | + | − | − | − | − | + | − | − | − | − | − | − | − | − | + | − | − |
| BIOS937 | − | + | − | − | − | + | − | − | − | − | − | − | − | + | + | − | + | − | + | − | − | + | − | − | − |
| BIOS940 | + | − | − | − | − | + | − | − | − | − | − | − | − | − | − | − | − | − | + | − | − | − | − | − | − |
| BIOS1006 | − | − | − | − | + | + | − | + | − | − | − | − | + | − | + | − | − | − | + | − | + | − | − | − | − |
| BIOS1049 | − | − | − | − | − | + | − | − | − | − | + | − | − | − | − | − | − | − | − | − | − | − | − | − | − |
| BIOS1079 | − | − | − | + | − | + | − | − | − | − | − | − | − | − | − | − | − | − | − | − | − | − | − | − | − |
| BIOS1099 | − | + | − | − | − | + | − | − | − | − | − | − | + | − | − | − | − | − | − | + | − | + | + | − | − |
| Discord (%)[c] | | 38 | 19 | 25 | 25 | 150 | 12 | 11 | 33 | 18 | 18 | 13 | 11 | 36 | 36 | 25 | 25 | 19 | 33 | 43 | 0 | 33 | 33 | 25 | 18 |

Note.
[a] "+" and "−", presence or absence of neuronatin signal.
[b] "+" indicates the present of the human chromosome, and "−" indicates the absence.
[c] Discord (%) = Discordant/Concordant × 100.
Discordant = neuronatin signal present/specified chromosome absent + neuronatin absent/specified chromosome present.
Concordant = neuronatin present/specified chromosome present + neuronatin absent/specified chromosome absent.

Localization of Neuronatin to Human Chromosome-20

The human-rodent somatic hybrid panel was screened to help localize human neuronatin gene. Twenty hybrid DNA samples containing different combinations of human chromosomes were used for PCR amplification with specific primers. In order to design the primers, the 3'-untranslated region of human (GenBank #U25034) and rat (GenBank #U08290) neuronatin cDNA was chosen as this was the least homologous region between the two species. A single product of 193 bp was predicted. This fragment was specifically amplified only from the two DNA samples containing chromosome-20, BIOS756 and BIOS940 (Table 4). None of the other 18 hybrid cell lines contained chromosome-20, and indeed, no products were amplified. These results conclusively localize, with 0% discordance, the neuronatin gene to chromosome-20.

Localization to the Long Arm of Chromosome-20

A series of deletions of human chromosome-20 were used for sub-chromosomal localization. These constructs were analyzed by PCR using the same neuronatin-specific primers and conditions described above. CF80–8, the hybrid cell line containing the 20q12–20q13 region of chromosome-20 did

Localization to Chromosome-20q11.2–12

FISH was used to confirm the results of the somatic panel mapping and to determine the copy number. Chromatographically purified lambda phage clone containing the full neuronatin genomic DNA clone was directly used as template to generate biotin-labeled probe and hybridize with human lymphocyte metaphase spreads. Several metaphase spreads were studied. Together with the results of G-banding, neuronatin gene was assigned, in single copy, to chromosome 20q11.2–12.

EXAMPLE 8

Neuronatin Genomic DNA

Using the human cDNA (SEQ ID No:5) as a probe, a human fetal brain genomic library (Stratagene) was screened. Three genomic clones were isolated. The human genomic sequence for neuronatin (SEQ ID No:6) was determined.

The complete sequence of human neuronatin gene is shown in FIG. 10. The gene spans 3973 bases and consists of three exons and two introns which encode two alternatively spliced mRNA isoforms, α and β and is deposited in GenBank (#U31767). The 5'-flanking region of neuronatin contains modified TATA and CAAT boxes, and a neural restrictive silencer element which governs neuron-specific expression.

Experimental Procedure

Based on an analysis of the sequences of human neuronatin cDNA isoforms and their mRNA on northern blotting, neuronatin mRNA was estimated to be about 1.2–1.3 kb in size. Consequently, the neuronatin gene would be predicted to be 4–10 kb, leading applicants to screen a lambda Fix II library (Stratagene, La Jolla, Calif.) containing 9–23 kb inserts of partially restricted Sau3AI fragments of human placental genomic DNA. As the total human genome contains about $3.0 \times 10^9$ bp, in order to obtain 1 or 2 positive clones, assuming neuronatin is in single copy, a minimum of 0.3 million individual plaques containing $2.7 \times 10^9$ to $6.9 \times 10^9$ bp (about 1–2 times the size of the human genome) would need screening. An aliquot (0.02 µl) of human genomic lambda FixII library, titer of $1.5 \times 10^{10}$ pfu/ml, was used to infect E.coli XL-Blue MRA strain (Stratagene) at 37° C. for 15 min in 15 ml of phage dilution buffer (50 mM Tris-Cl, 90 mM NaCl, 0.01% gelatin, pH 7.0), to an optical density of 0.35 at 590 nm. The host cells were pre-induced with 0.2% maltose overnight in LB medium containing 10 mM $MgSO_4$. The cell suspension was mixed with 200 ml of LB containing 0.7% agar, kept at 49° C., and poured onto 40 plates (φ10 cm) containing a base of 2% agar. Following incubation (37° C. for 18 hrs), the plaques measuring about φ1–2 mm were transferred onto nylon membrane. The membranes were then denatured in a solution containing 0.5 M NaOH and 1 M NaCl for 1 min, neutralized in 0.7 M phosphate buffer (pH 6.5) for 2 min and rinsed with 10×SSC (0.15 M sodium citrate, 1.5 M, pH 7.0). Thereafter, the membranes were UV-crosslinked (254 nm for 5 min) and used for hybridization with human neuronatin-β cDNA. The cDNA was $^{32}$P-labeled using random primer extension (Rediprime, Amersham, Arlington Heights, Ill.) and purified using Nick Columns (Amersham). Hybridization was carried out at 70° C. for 24 hrs with $1 \times 10^6$ cpm/ml of labeled probe (specific activity of $0.8 \times 10^9$ cpm/µg) in 200 ml of a solution containing 5×SSC, 1×Denhart's (0.02% Ficoll, 0.02% polyvinylpyrrolidone, 0.02% BSA),, 0.5% SDS and 200 µg/ml of denatured salmon sperm DNA. The blots were washed with 0.1% SDS for 1 hr and autoradiographed for 6 hrs without intensifying screens. As predicted, two plaques showing strong hybridization with the human neuronatin cDNA probe were identified.

Genomic DNA clones isolated by Southern hybridization may contain pseudogenes or highly homologous genes.[117, 119] Therefore, restriction digestion analysis was carried out to help distinguish them. Individual phage plaques were transferred into 20 µl of phage dilution buffer using pipette tips and mixed with 10 µl of overnight cultures of XL-Blue MRA strain. The suspension was used to inoculate 5 ml of LB medium containing 0.9% maltose and 5 mM $MgSO_4$ and incubated overnight at 37° C. with continuous shaking. A similar procedure was used for amplification in 300 ml. The released host DNA and RNA present in the phage-lysed solution was removed by incubation (37° C. for 2 hrs) with 5 mg RNase A and 500 U DNase I. Phage particles were precipitated using 12.5% PEG 8000 and 6.5 M NaCl at 0° C. for 1 hr and centrifugation (20,000×g for 30 min). Pellets were suspended in TE buffer (pH 8.0), traces of PEG and phage coat proteins were removed with chloroform and phenol. Following ethanol precipitation, phage DNA was dissolved in the same buffer. The DNA samples (5 µg), prepared from the two positive clones, were digested in separate reactions with EcoRI, BamHI, PstI, XhoI, HindIII and NotI. In some reactions combinations of enzymes were also used. The restriction fragments were separated on 1% agarose gel in TEE buffer (100 mM Tris-borate, 2 mM EDTA, pH 9.0), denatured with 0.5 M NaOH for 30 min, neutralized with 1 M Tris-Cl buffer (pH 7.5), transferred onto nylon with 1×SSC, rinsed with 2×SSC for 5 min and UV-crosslinked. The blots were hybridized with $1 \times 10^6$ cpm/ml of $^{32}$P-labeled neuronatin cDNA with a specific activity of $5 \times 10^8$ cpm/µg, at 65° C. for 5 hrs in a speed hybridization buffer containing 2×SSPE (20 mM $NaH_2PO_4$, 30 mM NaCl, 10 mM EDTA pH 7.4) , 7% PEG 8000 and 7% SDS. To reduce the amount of background signal, each blot was placed between pieces of Whatman filter paper during hybridization. The blots were washed with a solution containing 0.2×SSC and 0.1% SDS. The restriction pattern with both clones were similar. This suggested the absence of pseudogenes, and that comparable regions of the neuronatin gene were present in both phage clones.

Based on the above restriction analysis, a 6 kb BamHI fragment showing strong hybridization with human neuronatin-β cDNA was further characterized. When this fragment was gel-purified and digested with EcoRI, two fragments of 2.3 and 3.7 kb were generated. The 2.3 kb fragment hybridized with a probe generated from the 5'-end of neuronatin cDNA (a 141 bp PstI fragment from 5'-end of the human neuronatin-β cDNA), but not with a probe from the 3'-end of the cDNA (a 193 bp fragment of the 3'-end of neuronatin containing the poly(A) signal, generated by PCR using primers 5'-TGCGCCTCTACTGCACCGC-3' and 5'-CCCTGGTCTCATGCAGTTGTGG-3'). On the other hand, the 3.7 kb fragment hybridized with the 3'-end probe of human neuronatin cDNA, but not with the probe specific for the 5'-end. These results suggested the 6 kb BamHI fragment may contain the complete neuronatin gene; with the 2.3 kb BamHI-EcoRI fragment encoding the promoter and operator regions. Therefore, these two fragments (2.3 and 3.7 kb) were sub-cloned into pGEM7Zf(+) (Promega, Madison, Wis.) by white/blue selection on X-Gal LB plates.[80] Cycle sequencing with dideoxy-chain termination was carried out using the fmol-Sequencing System (Promega)[58]. The 5'-flanking region of the gene was sequenced by primer walking, beginning with the primer synthesized to be specific for the 5'-end of human neuronatin-β cDNA. About 1.5 kb of the upstream 5'-flanking region of the neuronatin gene was sequenced. Using a similar approach, the 3'-end of the gene was sequenced beginning with a primer that recognized the 3'-untranslated region of human neuronatin-β cDNA. Thereafter, the intervening region of the gene was sequenced by primer walking in both directions. The complete sequence of human neuronatin gene was 3973 bases long (FIG. 10).

As shown in FIG. 10, the promoter of human neuronatin gene contains a modified CAAT box, GGCGAAT at −59, and a modified TATA box, CATAAA at −27. The C of the prototypical CAAT box was substituted by G, and the first T of the canonical TATAAA box was replaced with C. Such modified or TATA-less promoters are known to be present in several other brain-specific genes including synapsin-I, aldolase C, neural cell adhesion molecule and olfactory neuron-specific protein.[127,131,135] The CATAAA box in the neuronatin promoter was identical to that seen in human aromatic L-amino acid decarboxylase gene which is another neuron-specific gene.[116,136]

Several putative transcription factor binding sites were found in the 5'-flanking region. These include consensus sequences for SP-1, AP-2 (two sites), δ subunit, SRE-2, NF-A1 and ETS. Neural restrictive silencer element (NRSE), with the consensus motif [TT(C/T)AG(C/A/T)ACC(A/G)CGGA(C/G)AG(T/C/A) (G/A)CC], determining neuron-specific gene expression, was present at −421 of the neuronatin gene. NRSE regions are present in genes which exhibit neuron-specific expression, such as synapsin-I, SCG10, Na/K-ATPase α 3-subunit and sodium channel-II.[86,88,95,134] The first intron of human neuronatin gene also contains binding sites for SP-1 and AP-3. Similar sites have been noted in the first intron of human ATP synthase α subunit[135] and human proto-oncogene c-myb.[129] Moreover, there are several unusual AT islands located in the first intron of neuronatin gene. There is increasing evidence indicating a regulatory role for the first intron in gene expression.[132]

Mapping of the transcription initiation site in human neuronatin gene was carried out by primer extension analysis of human fetal brain mRNA using a labeled oligonucleotide complementary to the region immediately preceding the start of the open reading frame. Only one reverse-transcribed cDNA product was; seen on primer extension. This identified a single transcription start site located 124 bases upstream from the methionine (ATG) initiation codon and 27 bases downstream from the modified TATA box. This is a typical distance between TATA box and mRNA transcription start site.[133]

The neuronatin gene contains three exons and two introns. All 5'- and 3'- splice sites matched with the consensus sequences.[120,125] The first exon has 195 bases and the second exon 81 bases, which are typical exon sizes in vertebrates.[121] The third exon has 1016 bases, somewhat larger than the average size of the last exon in vertebrates.[124,126] The putative branch point sequences TGCTAAA for intron 1 and TGCTATC for intron 2 were found between 25–35 bases upstream from the AG-3' cleavage sites of the introns. All introns of this gene conformed with GT/AG role.[123,125] No other exon- or intron-like structures were noted in the human neuronatin genomic DNA sequence.

The first exon, encoding 24 amino acids, contains the prototypical translation initiation site[38] in good context, GAACCATGG. Exon-2 encoded 27 amino acids and exon-3 encoded 30 residues. Based on the genomic structure, it is clear that the α-form of neuronatin mRNA, encoding a protein of 81 amino acid residues, is derived from all three exons. The β-form of neuronatin mRNA, encoding a protein of 54 amino acid residues, is derived from a combination of the first and third exons. These results imply that the α and β isoforms of human neuronatin mRNA were generated by differential splicing of the middle exon (exon-2). Interestingly, a putative α-helix transmembrane hydrophobic domain in the N-terminal of the deduced human neuronatin protein was entirely encoded by the first exon, and the highly basic hydrophilic domain at the C-terminal was encoded by exon-3. The middle exon was neither hydrophobic or hydrophilic.

Codon usage in the neuronatin gene was analyzed based on information derived from more than ten thousand genes present in the GenBank database.[137] The third nucleotide of all frequently used codons, except threonine, of neuronatin was noted to be either a G or C. The G+C% at the third nucleotide of a codon is believed to be important in determining codon usage in higher vertebrates.[118,128] The most frequently used codons in humans were found to be those with higher G+C% at their third nucleotide position. The high G+C% seen in the third nucleotide position of the neuronatin-codons are consistent with that expected for Homo sapiens. The neuronatin gene did not contain any codons for histidine or aspartic acid.

At the 3'-end of the neuronatin gene, a typical poly(A) signal and GT cluster were noted to be present. The poly(A) signal, AATAAA, was located 62 bases 5' to the poly(A) site, the usual distance being 15–20 bases. However, a GT-cluster was present, as would be expected, 5 bases downstream of the poly(A) site. The location of the GT-cluster was comparable to that seen in other genes such as human interferon, rabbit β-globin and mouse amy-1a.[122]

Throughout this application, various publications, including United States patents, are referenced by citation or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

1. Adams and Victor (1993) In: Principles of Neurology, 5th ed. McGraw-Hill, New York, pp 526–536.
2. Ball M. J. (1977) Neuronal loss, neurofibrillary tangles and granulovacuolar degeneration in the hippocampus with aging and dementia. Acta Neuropathol 27:111.
3. Benson et al. (1993) Nuc Acids Res 21, 2963–2965.
4. Buell and Coleman. (1979) Dendritic growth in the aged human brain and failure of growth in senile dementia. Science; 206:854.
5. Catania and Fairweater. (1991) DNA methylation and cellular aging. Mutation Res 256:283–293.
6. Chang Z. -F. and Chen K. -Y. (1988) Regulation of ornithine decarboxylase and other cell cycle-dependent genes during senescence of IMR-90 human diploid fibroblasts. J Biol Chem; 263:11431–11435.
7. Chomczynski and Sacchi. (1987) Anal Biochem 162, 156–159.
8. Clark J. M. (1988) Nuc Acids Res 16, 9677–9686.
9. Cohen et al. (1978) Age-associated pathological changes in male rats. Fed Proc; 37:2848–2850.
10. Coleman et al. (1977) J. Gerontol 32, 258–278.
11. Colman, et al. (1980) Brain poly(A)RNA during aging: stability of yield and sequence complexity in two rat strains. J. Neurochem 34:335–345.
12. Cotman, et al (1994) In: Basic Neurochemistry, 5th Edition, pp 607–626.
13. Crook et al. (1986) Age-associated memory impairment: Proposed diagnostic criteria and measures of clinical change - report of a National Institute of Mental Health Work Group. Dev Neuropsychol 2:261.
14. Crowley and Curtis. (1963) The development of somatic mutations in mice with age. Proc Natl Acad Sci USA 49:626–628.
15. Cutler R. G. Transcription of unique and reiterated DNA sequences in mouse liver and brain age tissues as a function of age. Exp Gerontol 1975; 10:37–60.
16. Dice J. F. Altered degradation of proteins microinjected into senescent human fibroblasts. J Biol Chem 1982; 257:14624–14627.
17. Finch C. E. Neuron atrophy during aging: programmed or sporadic. Trends Neurosci 1993; 16:104–110.
18. Finch C. E. In: Longevity, Senescence and the Genome. University of Chicago Press, 1990.

19. Finch C. E. Biochemistry of aging in the brain. In: Basic Neurochemistry, 5th ed, Siegel GJ, Agranoff BW, Albers RW, Molinoff PB, eds. Raven Press, New York, 1993.
20. Gabriel et al., in Child Neurology, 3rd Edition (1985) pp 189–270.
21. Goldman J., Cote L. In: Principles of Neural Science, 3rd ed, Kandel E. R., Schwartz J. H., Jessell T. M., eds. Appleton and Lange, Norwalk, 1991.
22. Goldspink and Kelly. Protein turnover and growth in the whole body, liver, and kidney of the rat from foetus to senility. Biochem J 1984; 217:507–516.
23. Gompertz B. On the nature of the function expressive of the law of human mortality and a new mode of determining the value of life contingencies. Phil Trans R Soc Lond 1825; 115:513.
24. Harley et al. Telomeres shorten during aging of human fibroblasts. Nature 1990; 345:458–460.
25. Harlow E., Lane D. Antibodies: A Laboratory Manual. Cold Spring Harbor Laboratory Publications, New York, 1988, pp53–137.
26. Hayflick L., Moorhead P. S. The serial cultivation of human diploid cell stains. Exp Cell Res 1961; 25:585–621.
27. Hayflick L. The cell biology of human aging. N. Engl. J Med 1976; 295:1302.
28. Hopp T. P. and Woods K. R. (1981) Proc Nat Acad Sci USA 78, 3824–3828.
29. Hughes K. A., Charlesworth B. A genetic analysis of senescence in Drosophila. Nature 1994; 367:64–66.
30. Jacobson, M. In: Developmental Biology, 3rd ed., pp4–93. Plenum Press, New York, (1991).
31. Jazwinski et al. A single gene change can extend yeast life span: The role of ras in cellular senescence. Adv Exp Med Biol 1993; 330:45–53.
32. Jendrisak et al. (1987) Meth Enzymol 152:359–371.
33. Joseph et al. (1993) Brain Res. 625, 244–255.
34. Kaplan R. M. Imagine no coronary artery disease. Circulation, 1991; 83:1452.
35. Kaufman, M. H. In: The Atlas of Mouse Development, pp5–8. Academic Press, London, (1992).
36. Kawasaki E. S. Amplification of RNA. In: PCR protocols: A Guide to Methods and Applications, Innis M. A., Gelfand D. H., Sninsky J. J., White T. J., eds. Academic Press, 1990, pp21–27.
37. Khan et al. (1991) Nuc Acids Res 19, 1715.
38. Kozak M. (1991) J Biol Chem 266, 19867–19870.
39. Kumar et al. Identification of a set of genes with developmentally down-regulated expression in the mouse Obrain. Biochem Biophys Res Commun 1992; 185:1155–1161.
40. Kuo et al. Biochem Biophy Acta 900, 10–16 (1987).
41. Lewin B. In: Genes V., Lewin B., ed., pp911–940. Oxford University Press, Oxford, (1994).
42. Liang P and Pardee AB. (1992) Science 257, 967–971.
43. Lichter et al. High-resolution mapping of human chromosome 11 by in situ hybridization with cosmid clones. Science 1990; 247:64–69.
44. Lomri et al. (1989) Gene 80, 87–98.
45. Lumpkin et al. Existence of high abundance antiproliferative mRNA's in senescent human diploid fibroblasts. Science 1986; 232:393–395.
46. Martin et al. Fibronectin and collagen gene expression during in vitro aging of pig skin fibroblasts. Exp Cell Res 1990; 191:8–13.
47. McCormick A, Campisi J. Cellular aging and senescence. Curr Opin Cell Biol 1991; 3:230–234.
48. Miller et al. Use of retroviral vectors for gene transfer and expression. Meth Enzymol 1993; 217:581–599.
49. Moment G. B. Theories of aging: an overview. In: Testing the Theories of Aging, Adelman R. C., Roth G. S., eds. Boca Raton, Fla., CRC, 1982, pp1–23.
50. Orgel L. E. The maintenance of the accuracy of protein synthesis and its relevance to aging. Proc Natl Acad sci USA 1963; 49:517–521.
51. Orita M., et al. Detection of polymorphisms of human DNA by gel electrophoresis as single-strand confirmation polymorphisms. Proc Natl Acad Sci USA 1989; 86:2766–2770.
52. Partridge L., Barton N. H. Optimality, mutation and the evolution of aging. Nature 1993; 362:305–311.
53. Pereira-Smith et al. Senescent and quiescent cell inhibitors of DNA synthesis. Exp Cell Res 1985; 160:297–306.
54. Rattan S. I. S. DNA damage and repair during cellular aging. Int Rev Cytol 1989; 116:47–88.
55. Riabowol et al. Transcription factor AP-1 activity is required for initiation of DNA synthesis and is lost during cellular aging. Proc Natl Acad Sci USA 1992; 89:157–161.
56. Richardson A, Cheung HT. The relationship between ages-related changes in gene expression, protein turnover, and the responsiveness of an organism to stimuli. Life Sci 1982; 31:605–613.
57. Sambrook et al., Molecular Cloning: A Laboratory Manual, Cold Springs Harbor, N.Y., 1989, pp 9.31–57 and 18.60–75
58. Sanger et al. (1977) Proc Natl Acad Sci USA 74, 5463–5467.
59. Sapolsky R. M., Ed., Stress, the Aging Brain, and the Mechanisms of Neuron Death (MIT Press, Cambridge, Mass., 1992, pp 30).
60. Scheibel et al. Progressive dendritic changes in aging human cortex. Exp Neurol 1975; 47:392.
61. Seshadri T., Campisi J. Repression of c-fos transcription and an altered genetic program in senescent human fibroblasts. Science 1990; 247:205–209.
62. Stein et al. Senescent cells fail to express cdc2, cycA, and cycB in response to mitogen stimulation. Proc Natl Acad Sci USA 1991; 88:11012–11016.
63. Stella AMG, Lajtha A. Macromolecular turnover in brain during aging. Gerontology 1987; 33:136–148.
64. Strehler et al. Codon-restriction theory of aging and development. J Theor Biol 1971; 33:429–474.
65. Wahle E., Keller W. (1992) Ann Rev Biochem 61, 419–440.
66. Wang E. Rapid disappearance of statin, a nonproliferating and senescent cell-specific protein, upon reentering the process of cell cycling. J Cell Biol 1985; 101:1695–1702.
67. Wang E., Tomaszewski G. Granular presence of terminin is the marker to distinguish between senescent and quiescent states. J Cell Physiol 1991; 147:514–522.
68. Welsh et al. (1992) Nuc Acids Res 20, 4965–4970.
69. Zs-Nagy I, Nagy K. On the role of cross-linking of cellular proteins in aging. Mech Aging Dev 1980; 14:245–251.
70. Adams and Rose, Structural requirements of a membrane- spanning domain for protein anchoring and cell surface transport. *Cell* 41 (1985) 1007–1015.
71. Adunyah, et al, Structural and functional comparison of a 22 kDa protein from internal human platelet membranes with cardiac phospholamban. *Biochim Biophys Acta* 941 (1988) 63–70.
72. Barnes, et al, Kilo-sequencing: creation of an ordered nest of asymmetric deletions across a large target sequence carried on phage M13. *Meth Enzymol* 101 (1983) 98–122.

73. Brandt, et al, Ring chromosome 20 with loss of telomeric sequences detected by multicolor PRINS. *Clin Genet* 44 (1993) 26–31.
74. Brown-Schimer, et al, Molecular cloning & chromosome mapping of the human gene encoding protein phosphotyrosyl phosphatase 1B. *Proc Natl Acad Sci USA* 87 (1990) 5148–5152.
75. Cherif, et al, Detection of single copy genes by nonisotopic in situ hybridization on human chromosomes. *Hum Genet* 81 (1989) 358–362.
76. Christy and Nathans, DNA binding site of the growth factor-inducible protein zif268. *Proc Nat Acad Sci USA* 86 (1989) 8737–8741.
77. Cotter, et al, Deletion of the long arm of chromosome 20 in a patient with small cell lymphocytic lymphoma. *Cancer Genet Cytogenet* 70 (1993) 142–143.
78. Davis, et al, Hematologic manifestations associated with deletions of the long arm of chromosome 20. *Cancer Genet Cytogenet* 12 (1984) 63–71.
79. Diez-Martin, et al, Chromosome studies in 104 patients with polycythemia vera. *Mayo Clin Proc* 66 (1991) 287–299.
80. Ey, et al, Giardia intestinalis: detection of major genotypes by restriction analysis of gene amplification products. *Int J Parasitol* 23 (1993) 591–600.
81. Faust, et al, Two proteolipids and dolichol-linked oligosaccharides accumulate in motor neuron degeneration mice (mnd/mnd), a model for neuronal ceroid lipofuscinosis. *J giol Chem* 269 (1994) 10150–10155.
82. Fearnley, et al, The sequence of the major protein stored in ovine ceroid lipofuscinosis is identical with that of the dicyclohexylcarbodiimide-reactive proteolipid of mitochondrial ATP synthase. *Biochem J* 268 (1990) 751–758.
83. Hendricks-Taylor, et al, The CCAAT enhancer binding protein (c/EBPα) gene (CEBPA2) maps to human chromosome 19q19.1 and the related nuclear factor NF-IL6 (c/EBPβ gene C/EBPB) maps to human chromosome 20q13.1. *Genomics* 14 (1992) 12–17.
84. Henikoff, S., Unidirectional digestion with exonuclease III creates targeted breakpoints for DNA sequencing. *Gene* 28 (1984) 351–359.
85. Joseph, et al, Neuronatin mRNA: Alternatively spliced forms of a novel brain-specific mammalian developmental gene. *Brain Res* 690 (1995) 92–98.
86. Kraner, et al, Silencing the type II sodium channel gene: a model for neural-specific gene regulation. *Neuron* 9 (1992) 37–44.
87. Krunze, et al, Localization of the active type I DNA topoisomerase gene in human chromosome 20q11.2–13.1 and two pseudogenes on chromosomes 1q23—23 and 22q11.2–13.1. *Hum Genet* 84 (1989) 6–10.
88. Li, et al, Identification of a functional silencer element involved in neuron-specific expression of the synapsin-I gene. *Proc Natl Acad Sci USA* 90 (1993) 1460–1464.
89. Mandel, et al, cDNA sequence encoding the 16-kDa proteolipid of chromaffin granules implies gene duplication in the evolution of $H^+$-ATPases. *Proc Natl Acad Sci USA* 85 (1988) 5521–5524.
90. Mercer, et al, Molecular cloning and immunological characterization of the γ-polypeptide, a small protein associated with Na, K-ATPase. *J Cell Biol* 121 (1993) 579–586.
91. Mierendorf and Pfeffer, Direct sequencing of denatured plasmid DNA. *Meth Enzymol* 152 (1987) 556–562.
92. Mohandas, et al, Regional localization of the human genes for S-adenosyl-homocysteine hydrolase (cen→Q13) and adenosine deaminase (Q13→qter) on chromosome 20. *Hum Genet* 66 (1984) 292–295.
93. Moorman, et al, Unitary anion currents through phospholemman channel molecules. *Nature* 377 (1995) 737–740.
94. Moorman, et al, Phospholemman expression induces a hyperpolarization-activated chloride current in Xenopus oocytes. *J Biol Chem* 267 (1992) 14551–14554.
95. Mori, et al, A cell type-specific silencer element that controls the neural-specific expression of the SCG10 gene. *Neuron* 4 (1990) 583–594.
96. Morris, et al, Localization of the SRC oncogene to chromosome band 20q11.2 and loss of this gene with deletion (20q) in two leukemic patients. *Blood* 74 (1989) 1768–1773.
97. Navarre, et al, Two distinct genes encode small isoproteolipids affecting plasma membrane $H^+$-ATPase activity of *Saccharomyces cerevisiae*. *J Biol Chem* 269 (1994) 21262–21268.
98. Navarre, et al, A proteolipid associated with the plasma membrane $H^+$-ATPase of fungi. *Ann NY Acad Sci* 671 (1992) 189–194.
99. Navarre, et al, Purification and complete sequence of a small proteolipid associated with the plasma membrane $H^+$-ATPase of Saccharomyces cerevisiae. *J Biol Chem* 267 (1992) 6425–6428.
100. Nieto, et al, A receptor protein kinase implicated in the segmental patterning of the hindbrain and mesoderm. *Development* 116 (1992) 1137–50.
101. Palmer, et al, Purification and complete sequence determination of the major plasma membrane substrate for cAMP-dependent protein kinase and protein kinase C in myocardium. *J Biol Chem* 266 (1991) 11126–11130.
102. Palmer, et al, Mitochondrial ATP synthase subunit c storage in the ceroid-lipofuscinoses (Batten Disease). *Am J Med Genet* 42 (1992) 561–567.
103. Pinkel, et al, Cytogenetic analysis using quantitative I high sensitivity, fluorescence hybridization. *Proc Natl Acad Sci USA* 83 (1986) 2934–2938.
104. Quintrell, et al, Identification of a human gene (HCK) that encodes a protein-tyrosine kinase and is expressed in hemopoietic cell. *Mol Cell Biol* 7 (1987) 2267–2275.
105. Simmerman, et al, Sequence analysis of phospholamban, identification of phosphorylation sites and two major structural domains. *J Biol Chem* 261 (1986) 13333–13341.
106. Suzuki and Wang, Stimulation of bovine cardiac sarcoplasmic reticulum $Ca^{2+}$ pump and blocking of phospholamban phosphorylation and dephosphorylation by a phospholamban monoclonal antibody. *J Biol Chem* 261 (1986) 7018–7023.
107. Tada, Molecular structure and function of phospholamban in regulating the calcium pump from sarcoplasmic reticulum. *Ann NY Acad Sci* 671 (1991) 92–103.
108. Tanford, The hydrophobic effect and the organization of living matter. *Science* 200 (1978) 1012–1018.
109. Thiel, et al, Regulation of synapsin I gene expression by the zinc finger transcription factor zif268/egr-1. *J Biol Chem* 269 (1994) 15294–15301.
110. Verma and Babu, In: *Human Chromosomes: Manual of Basic Techniques*. Pergamon, New York, 1989.
111. Wawrzynow, et al, Sarcolipin, the "proteolipid" of skeletal muscle sarcoplasmic reticulum, is a unique, amphipathic, 31-residue peptide. *Arch Biochem Biophys* 298 (1992) 620–623.
112. White, et al, Deletion of chromosome 20q in myelodysplasia can occur in a multipotent precursor of both myeloid cells and B cells. *Blood* 83 (1994) 2809–2816.
113. Wijnholds, et al, Segment-specific expression of the neuronatin gene during early hindbrain development. *Dev Biol* 171 (1995) 73–84.

114. Wilkinson, et al, Segment-specific expression of a zinc-finger gene in the developing nervous system of the mouse. *Nature* 337 (1989) 461–464.
115. Zasloff, et al, A new method for the purification and identification of covalently closed circular DNA molecules. *Nuc Acids Res* 5 (1978) 1139–1152.
116. Albert, et al. (1992). Distinct promoters direct neuronal and nonneuronal expression of rat aromatic L-amino acid decarboxylase. *Proc. Natl. Acad. Sci. USA* 89: 12053–12057.
117. Akiyama, et al. (1994). Gene structure and cell type-specific expression of the human ATP synthase α subunit. *Biochim. Biophys. Acta* 1219: 129–140.
118. Aota and Ikemura. (1986). Diversity in G+C content at the third position of codons in vertebrate genes and its cause. *Nuc. Acids Res.* 14: 6315–6355.
119. Aqua, et al. (1991). Characterization and expression of a cDNA specifying subunit VIIc of bovine cytochrome c oxidase. *Gene* 104: 211–217.
120. Balvay, et al. (1993). Pre-mRNA secondary structure and the regulation of splicing. *Bioessays* 15: 165–169.
121. Berget, S. (1995). Exon recognition in vertebrate splicing. *J. Biol. Chem.* 270: 2411–2414.
122. Birnstiel, et al. (1985). Transcription termination and 3'processing: the end is in site! *Cell* 41: 349–359.
123. Breathnach and Chambon. (1981). Organization and expression of eukaryotic split genes coding for proteins. *Annu. Rev. Biochem.* 50: 349–383.
124. Brunak, et al. (1991). Prediction of human mRNA donor and accepter sites from the DNA sequence. *J. Mol. Biol.* 220: 49–65.
125. Green, M. R. (1991). Biochemical mechanisms of constitutive and regulated pre-mRNA splicing. *Annu. Rev. Cell Biol.* 7: 559–599.
126. Hawkins, J. D. (1988). A survey on intron and exon lengths. *Nuc. Acids Res.* 16: 9893–9908.
127. Hirsch, et al. (1990). Identification of positive and negative regulatory elements governing cell-type-specific expression of the neural cell adhesion molecule gene. *Mol. Cell Biol.* 10: 1959–1968.
128. Ikemura, T. (1985). Codon usage and tRNA content in unicellular and multicellular organisms. *Mol. Biol. Evol.* 2: 13–34.
129. Jacobs, et al. (1994). Identification of a second promoter in the human c-myb proto-oncogene. *Oncogene* 9: 227–235.
130. Kudrycki, et al. (1993). Olf-1-binding site: characterization of an olfactory neuron-specific promoter motif. *Mol. Cell Biol.* 13: 3002–3014.
131. Makeh, et al. (1994). Analysis of a brain-specific isozyme. Expression and chromatin structure of the rat aldolase C gene and transgenes. *J. Biol. Chem.* 269: 4194–4200.
132. Makino, et al. (1994). Cloning and characterization of a c-myc intron binding protein (MIBP1). *Nuc. Acids Res.* :22: 5679–5685.
133. Maniatis, et al. (1987). Regulation of inducible and tissue-specific gene expression. *Science* 236: 1237–1245.
134. Pathak, et al. (1994). The presence of both negative and positive elements in the 5'-flanking sequence of the rat Na, K-ATPase α3 subunit gene are required for brain expression in transgenic mice. *Nuc. Acids Res.* 22: 4748–4755.
135. Sauerwald, et al. (1990). The 5'-flanking region of the synapsin I gene. *J. Biol. Chem.* 265: 14932–14937.
136. Van Thai, et al. (1993). Identification of a neuron-specific promoter of human aromatic L-amino acid decarboxylase gene. *Mol. Brain Res.* 17: 227–238.
137. Wada, et al. (1990). Codon usage tabulated from the GenBank genetic sequence data. *Nuc. Acids Res.* 18: 2367–2411.
138. Becker et al., "Use of recombinant adenovirus for metabolic engineering of mammalian cells" Methods in Cell Biology, 43:161–189 (1994).
139. Bett et al., "An efficient and flexible system for construction of adenovirus vectors with insertions or deletions in early regions 1 and 3" Proceedings of the National Academy of Sciences USA, 91:8802–8806 (1994).
140. Krougliak and Graham, "Development of cell lines capable of complementing E1, E4 and protein IX defective adenovirus type 5 mutants" Human Gene Therapy, 6:1575–1586 (1995).
141. Morsy et al., "Efficient adenoviral vector mediated ornithine transcarbamylase expression in deficient mouse and human hepatocytes" Journal of Clinical Investigation, 92:1580–1586 (1993).

What is claimed is:

1. A purified, isolated and cloned nucleic acid which has a genomic DNA sequence as set forth in SEQ ID NO:6 or a cDNA sequence as set forth SEQ ID NO:5.

2. A vector which comprises the DNA of claim 1.

3. A host cell transformed with the vector of claim 2.

4. A DNA construct comprising genomic DNA or cDNA as set forth in claim 1 ligated into the vector pLXSN.

5. A host cell transfected with the construct of claim 4.

6. A host cell as set forth in claim 5 wherein said host cell is selected from the group consisting of NIH3T3 and LaN1.

7. An isolated and purified rat cDNA having a nucleotide sequence as set forth in SEQ ID NO:1, designated neuronatin-α.

8. An isolated and purified rat cDNA having a nucleotide sequence as set forth in SEQ ID NO:2, designated neuronatin-β.

9. A vector which comprises the cDNA of claims 7 or 8.

10. A host cell which is transformed with the vector of claim 9.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 1195 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
GCGAACCCTT  GCTCTCGACC  ACCCACCCAC  TTTCGGAACC  ATGGCCGCAG  TGGCAGCAGC        60

CTCGGCAGAA  CTGCTCATCA  TCGGCTGGTA  CATCTTCCGC  GTGCTGCTGC  AGGTGTTCCT       120

GGAATGCTGC  ATTTACTGGG  TAGGATTCGC  TTTTCGAAAT  CCTCCAGGGA  CACAGCCCAT       180
```

```
TGCGAGAAGT GAGGTGTTCA GGTACTCCCT GCAGAAGCTG GCGCACACGG TGTCCCGGAC      240

CGGGCGGCAG GTGCTGGGGG AGCGCAGGCA CCGAGCCCCC AACTGAGGCC CCATCTCCCA      300

GCCCTGGGCG CCGTGTCAT  CAGGTGCTCC TGTGCTTCTC GACCAGCATG GGAGCCAATG      360

CCGCGCAGGA ATGGGGGTC  CCCTGTGCTC CCTCGTCAGA GGAGCACTTG CCAAGGTCAG      420

TGAGGGGCCG GTAGGTCCCC AGAAAAGCAG CACCGACAAT GATGAAGACA TCAGTTCCTT      480

TCCCAGCCCC CCCCCCCTTT GCCCCTGTCC CATGGCCGGC GGGTGGGAGA GGATGGGGGA      540

AGAGGGGAGC AACCCTCGAG ATATGGGCGT AGGCACCACA TTCTGATCTG GACCAAGTTG      600

GAACAGCACC ATCTCAGCCG CACAGATCCT ACCATGGAGA GCTAACACCC CACCAACCAG      660

CAGAATGGAC ATTCTGACAT CACCAGCTGA ACCCTGAAT  CTCGGTGCAG AAGAGAAAGT      720

GTCAACTGCG TGCAGCACTG GGGGAGTGGA GGGTGTGGGT GGTGGAGGAA GAGGGTTAAG      780

AAAACTAGTG GGGCCCTCTT GCTGTCCCTT GCCTATGGCA CGCATATTCC TGCCTTGCTC      840

CCTCACTCCC CCTCTCCCCT GCCTTCCAAA GCCCCACCCC CCAAAAATGT GTCACTTGAT      900

TCGGACCTAT TCAACCAGTA ATTGGATCCC ACCTTTACCA AAACACCGTC TCTGACCCCC      960

GGCCCTTCAC TGATCTTGCT TATCCCTGGT CTCACGCAGC AGTTGTGGTT GCTATTGTGG     1020

TAGTCGCTAA TTGTACTAGT TTACGTGTGC ATTAGTTGTG TCTCCCCGGC TAGATTGTAA     1080

GCTCCTGGAG ACAGGGACCA CCTCCACAAA AAATAAAAAA ACGGACCTCT CCTGTCTTGT     1140

AGTGTGCTAG GACCCTGCAG GGCAGTGGGG GTGCACCAAA AAAAAAAAAA AAAAA         1195
```

( 2 ) INFORMATION FOR SEQ ID NO:2:

( i ) SEQUENCE CHARACTERISTICS:
        ( A ) LENGTH: 1113 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

```
GCGAACCCTT GCTCTCGACC ACCCACCCAC TTTCGGAACC ATGGCCGCAG TGGCAGCAGC       60

CTCGGCAGAA CTGCTCATCA TCGGCTGGTA CATCTTCCGC GTGCTGCTGC AGGTGTTCAG      120

GTACTCCCTG CAGAAGCTGG CGCACACGGT GTCCCGGACC GGGCGGCAGG TGCTGGGGGA      180

GCGCAGGCAC CGAGCCCCCA ACTGAGGCCC CATCTCCCAG CCCTGGGCGG CCGTGTCATC      240

AGGTGCTCCT GTGCTTCTCG ACCAGCATGG GAGCCAATGC CGCGCAGGAA TGGGGGGTCC      300

CCTGTGCTCC CTCGTCAGAG GAGCACTTGC CAAGGTCAGT GAGGGGCCGG TAGGTCCCCA      360

GAAAAGCAGC ACCGACAATG ATGAAGACAT CAGTTCCTTT CCCAGCCCCC CCCCCTTTG      420

CCCCTGTCCC ATGGCCGGCG GGTGGGAGAG GATGGGGGAA GAGGGGAGCA ACCCTCGAGA      480

TATGGGCGTA GGCACCACAT TCTGATCTGG ACCAAGTTGG AACAGCACCA TCTCAGCCGC      540

ACAGATCCTA CCATGGAGAG CTAACACCCC ACCAACCAGC AGAATGGACA TTCTGACATC      600

ACCAGCTGAA ACCCTGAATC TCGGTGCAGA AGAGAAAGTG TCAACTGCGT GCAGCACTGG      660

GGGAGTGGAG GGTGTGGGTG GTGGAGGAAG AGGGTTAAGA AAACTAGTGG GGCCCTCTTG      720

CTGTCCCTTG CCTATGGCAC GCATATTCCT GCCTTGCTCC CTCACTCCCC CTCTCCCCTG      780

CCTTCCAAAG CCCCACCCCC CAAAAATGTG TCACTTGATT CGGACCTATT CAACCAGTAA      840

TTGGATCCCA CCTTTACCAA AACACCGTCT CTGACCCCCG GCCCTTCACT GATCTTGCTT      900

ATCCCTGGTC TCACGCAGCA GTTGTGGTTG CTATTGTGGT AGTCGCTAAT TGTACTAGTT      960
```

```
TACGTGTGCA TTAGTTGTGT CTCCCCGGCT AGATTGTAAG CTCCTGGAGA CAGGGACCAC    1020

CTCCACAAAA AATAAAAAAA CGGACCTCTC CTGTCTTGTA GTGTGCTAGG ACCCTGCAGG    1080

GCAGTGGGGG TGCACCAAAA AAAAAAAAAA AAA                                 1113
```

( 2 ) INFORMATION FOR SEQ ID NO:3:

( i ) SEQUENCE CHARACTERISTICS:
        ( A ) LENGTH: 81 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Met Ala Ala Val Ala Ala Ala Ser Ala Glu Leu Leu Ile Ile Gly Trp
  1               5                  10                  15

Tyr Ile Phe Arg Val Leu Leu Gln Val Phe Leu Glu Cys Cys Ile Tyr
             20                  25                  30

Trp Val Gly Phe Ala Phe Arg Asn Pro Pro Gly Thr Gln Pro Ile Ala
         35                  40                  45

Arg Ser Glu Val Phe Arg Tyr Ser Leu Gln Lys Leu Ala His Thr Val
     50                  55                  60

Ser Arg Thr Gly Arg Gln Val Leu Gly Glu Arg Arg His Arg Ala Pro
 65                  70                  75                  80

Asn
```

( 2 ) INFORMATION FOR SEQ ID NO:4:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Ala Ala Val Ala Ala Ala Ser Ala Glu Leu Leu Ile Ile Gly Trp
  1               5                  10                  15

Tyr Ile Phe Arg Val Leu Leu Gln Val Phe Arg Tyr Ser Leu Gln Lys
             20                  25                  30

Leu Ala His Thr Val Ser Arg Thr Gly Arg Gln Val Leu Gly Glu Arg
         35                  40                  45

Arg His Arg Ala Pro Asn
     50
```

( 2 ) INFORMATION FOR SEQ ID NO:5:

( i ) SEQUENCE CHARACTERISTICS:
        ( A ) LENGTH: 704 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
CTCAAGAGTG AAGACAAGGT CAAGGCCATT GCCAACCTGT ACGGCCCCCT GATGGCGCTG     60

AACCACATGG TGCAGCAGGA CTATTTCCCC AAGGCCCTTG CACCCTGCT GCTGGCGTTC    120

GTGACCAAGC CCAACAGCGG ACTCCGAGAC CAGCGGATCT CGGCAAACCC TCTTTCTCGA   180
```

|  |  |  |  |  |  |
|---|---|---|---|---|---|
| CCACCCACCT | ACCATTCTTG | GAACCATGGC | GGCAGTGGCG | GCGGCCTCGG | CTGAACTGCT | 240 |
| CATCATCGGC | TGGTACATCT | TCCGCGTGCT | GCTGCAGGTG | TTCAGGTACT | CCCTGCAGAA | 300 |
| GCTGGCATAC | ACGGTGTCGC | GGACCGGGCG | GCAGGTGTTG | GGGGAGCGCA | GGCAGCGAGC | 360 |
| CCCCAACTGA | GGCCCCAGCT | CCCAGCCTGG | GCGGCCGTAT | ATAGTGCTCC | TGTGCATCTC | 420 |
| GGCCAGCACG | GGAGCCAGTG | CCGCGCAGGA | ATGTGGGGTC | CCCTGTGTTC | CCTCGCCAGA | 480 |
| GGAGCACTTG | GCAAGGTCAG | TGAGGGGCCA | GTAGACCCCC | GGAGAAGCAG | TACCGACAAT | 540 |
| GACGAAGATA | CCAGATCCCT | TCCCAACCCC | TTTGCACCGG | TCCCACTAAG | GGGCAGGGTC | 600 |
| GAGAGAGGAG | GGGGATAGG | GGGAGCAGAC | CCTGAGATCT | GGGCATAGGC | ACCGCATTCT | 660 |
| GATCTGGACA | AAGTCGGGAC | AGCACCATCC | CAGCCCCGAA | GCCA |  | 704 |

( 2 ) INFORMATION FOR SEQ ID NO:6:

( i ) SEQUENCE CHARACTERISTICS:
        ( A ) LENGTH: 3973 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

|  |  |  |  |  |  |  |
|---|---|---|---|---|---|---|
| GGATCCTGAG | GCAGCTACAG | CCTCGAAATA | TTTTAAGATG | GCAGCCTAGG | CTAAGCTTGC | 60 |
| CTTTTTCAAA | CAGCCCAGCG | TCACTTTGCC | AGAATCTGCC | AACTTCTCCG | AAAGTCAATG | 120 |
| TAGAAAAAAA | GTCACTATGC | TACTTTGTCC | AAACTGAACT | CGTTTGGATC | ATTACACCTC | 180 |
| CATCTGCTGC | TGGCACTGTA | CAGAACCTGA | CCTCTGGGAG | CTTTTAATGA | AAATTAATTT | 240 |
| TCTATCCACA | TAGGGGCAAA | TGCCAGTTGG | TCCCTGGGCC | AGGCAGCTTG | CTGGAAAGAG | 300 |
| GTGCTTTCGG | CTAGCTACCG | GTGCGCGGGG | ACCACACTCA | CAAACCGCAT | TCCGGTCTTC | 360 |
| CCGCCCGAAA | ATCCGCGCTG | TGCGAGGGAC | CCACAAGACT | GGCGGTCTAA | AAGGGACCCG | 420 |
| CCTCACTTGG | AAACGGGGCT | GCGGTAGCAC | AACCCTCCGG | TAGCGGTAGG | TAACCCCGTT | 480 |
| CGGTGATCCA | GCCGCACAGC | GCAACGGGTA | CAAAGAACCC | CACTGGCTAA | GGCCGACCTA | 540 |
| CCAGGGCTTG | GGGGAGGGGA | GCGGAAGACT | GAGGTCGAAA | CGACCTGTCC | AGCAGAAAAC | 600 |
| TATCCCCAAG | CATATTCCAA | CCACTTCTCC | GTAGAGCTCA | TTCCTTCCGT | GCATACGAAG | 660 |
| GGCGCCAATC | CTTCCTGTAT | CCCTCCCACA | GTACCGGGTG | ACTACTGCTT | TGCGCCCAA | 720 |
| AGCGCAGTGC | TCTGGCTCAG | CTCCCTACAG | TAGCGACCTC | CACCGCAGAT | TCTCATCTCC | 780 |
| TCGCTACCGT | AAGAGAGATG | TAAAGAATCA | GACGGGTTAC | GCGCTCAGGC | ACCCTCATGA | 840 |
| AGCAGAGGAC | CTGGGCTTAA | AACTCATTCA | GTATTAGGAA | AAGAGCGCCG | AGCACGGGCC | 900 |
| TATTATGCCA | AAGCTTCTGA | AAGGGGCACC | ACGTTTTTG | CTCTATGGGG | CAGATGACCC | 960 |
| CTCCCTAATT | TCGGTTTTCC | ATCCATCCCC | AAGGTAGGCT | TTGGAGTGGC | ACCGGAGACT | 1020 |
| GAGCTCAAAT | TTGCAGGCCA | GGGACTGGGG | AGAAGGGCGC | CACACTAAGA | GACCTGCACC | 1080 |
| CCCATTCTCG | CCCTGTACTC | TACCCAGAGT | CGTGGTACCC | CTCCATTTTA | AAGCAAAATC | 1140 |
| CAAAAGCAAG | CACGGCGGAA | TCTTCTGGAA | GGGGCTAAG | ATGGAACTCA | GGAGGCGGGG | 1200 |
| GTCGGTATGG | AAAGAGCAGA | TGGATTATTT | TTTTCCTCTC | CTGGCGAATG | AGGAGCGCCC | 1260 |
| CCAGCCACCC | CTCCTCATAA | ACACCCCCA | AGGCGCGCAT | GCGCACTTAG | GTGGCGGGCG | 1320 |
| GGTACTTAAG | GCGCGGCCAC | CGGGCTGGCA | GTGCGCCCAA | CAGCGGACTC | CGAGACCAGC | 1380 |
| GGATCTCGGC | AAACCCTCTT | TCTCGACCAC | CCACCTACCA | TTCTTGGAAC | CATGGCGGCA | 1440 |
| GTGGCGGCGG | CCTCGGCTGA | ACTGCTCATC | ATCGGCTGGT | ACATCTTCCG | CGTGCTGCTG | 1500 |

```
CAGGTAAGTC TGACGGGGTT TCGGGTTTCG GGTGGGATAG GGTTCCCAAC TCGCGCCCCT 1560
AGAACCCGCA AGACTGCGTC GCGATTGCCG CTTCCCGGAC CCGTCCTATT CCGATTGCCG 1620
CGATCCTTGC CTGCCCTTGT GCCGCTGCCG GCACCGCGCG CCCCCTGCCC ATTCCCTGCG 1680
CCGTCCTCCT CGCGCTGACC CTCCCTAGTG CGCCCGCGCC TGCCAGGGAA CAAAGACTCG 1740
GGGCGCGGCG GGCGACCGCT GCGGACGATC ACCCAGGCAT TTAGCGACCT ACGCGGTAAG 1800
AAAAACCCGC TACACCCGGA CTCGACCCCA GGAGGGAGGC GGGGCACTAC TGTGTTGAAA 1860
GACTTTACAG CTCGCAGAGT GAAAATTTTC CACCTTAAAA AATTGCGCAT GCGGAGAAA 1920
TTTTATTTAA AAAAACATAT AGCGCTTGCG GGGGTGGAAC AAAAAATAAG TTAGAAAAG 1980
GCACTTCTCA GAAAAAATAA AAATTACTTC GCAAAAAAAA AAAAAACCCT ACAACGAATT 2040
AGAGAAAAAG TAGTTCACAC CAAACAGAA AAACGCGCAT TGCAGGAAAA ATAAATCGGA 2100
GAAAAGCACT TGGCAGAAAA AAATGCATTA GATTAAAAAC GCACTGCAGA AAAAAATTAG 2160
ACAAGGGAGC TAACGGAAAA AAATGGATCG GGCCAAAAAC GCTTTAAAGA AAAAAATTAG 2220
AGGAAAAAGC CCCTCGCGCG AAAAATAGAA GGGGAAAAAA AGCACTTCCA AAAAAGGACA 2280
ATTGCTTTAC AAAAAAAAAA AATAATAATA AAAAAAAATA AAAAGAGGC AAAAGCGCTT 2340
GGTGTAAAAA GAGATAAATC AGAAGAAAGC GCTTTGCCCA TAAAATCATT TACCCTAAAA 2400
GCTCCCTTTG CAGGAAGAAT TCCTGCTAA AGGAATCCTT TGCCAAAGGA ATCGCATATT 2460
TCCTTCAAGG TGTTCCTGGA ATGCTGCATT TACTGGGTAG GATTCGCTTT TCGAAATCCT 2520
CCAGGGACAC AGCCCATTGC GAGAAGTGAG GTATACCTAA GTTGTGGGTC CAATCAGCTT 2580
GCCGCCATGC AGCTCTCAGC ACAGTTGGAA AAGCTCCAGC TGCCCTGACT CGTGGACAAC 2640
TGCGCCCGCG CCCCGCCTCT CCAGCCTACG CTGAGTGGGC GGGCGGGGCA GGGGGTGGGG 2700
CGGGGGTGGG CACGGCAGCA CCACAGACAT GCTGTGGGTG CTATCCACTA AGGGTGGGTC 2760
CTGGGTTTCT CGTCGCAGGT GTTCAGGTAC TCCCTGCAGA AGCTGGCATA CACGGTGTCG 2820
CGGACCGGGC GGCAGGTGTT GGGGGAGCGC AGGCAGCGAG CCCCCAACTG AGGCCCCAGC 2880
TCCCAGCCCT GGGCGGCCGT ATCATCAGGT GCTCCTGTGC ATCTCGGCCA GCACGGGAGC 2940
CAGTGCCGCG CAGGAATGTG GGTCCCCTG TGTTCCCTCG CCAGAGCACT TGGCAAGGTC 3000
AGTGAGGGGC CAGTAGACCC CCGGAGAAGC AGTACCGACA ATGACGAAGA TACCAGATCC 3060
CTTCCCAACC CCTTTGCACC GGTCCCACTA AGGGCAGGG TCGAGAGAGG AGGGGGGATA 3120
GGGGGAGCAG ACCCTGAGAT CTGGGCATAG GCACCGCATT CTGATCTGGA CAAAGTCGGG 3180
ACAGCACCAT CCCAGCCCCG AAGCCCGGGC CATGCCAGCA GGCCCCACCA TGGAAATCAA 3240
AACACCGCAC CAGCCAGCAG AATGGACATT CTGACATCGC CAGCCGACGC CCTGAATCTT 3300
GGTGCAGCAC CCACCGCGTG CCTGTGTGGC GGGACTGGAG GGCACAGTTG AGGAAGGAGG 3360
GTGGTTAAGA AATACAGTGG GGCCCTCTCG CTGTCCCTTG CCCAGGGCAC TTGTATTCCA 3420
GCCTCGCTGC ATTTGCTCTC TCGATTGCCC CTTTCCTCCT ACATGCCTCC CAAGCCCACC 3480
CTACTCCAAA AGTAATGTGT CACTTGATTT GGAACTATTC AAGCAGTAAA AGTAAATGAA 3540
TCCCACCTTT ACTAAAACAC TTTCTCTGAA CCCCCCTTGC CCCTCACTGA TCTTGCTTTT 3600
CCCTGGTCTC AGCAGTTGTG GTCAATATTG TGGTAATCGC TAATTGTACT GATTGTTTAA 3660
GTGTGCATTA GTTGTCTCTC CCCAGCTAGA TTGTAAGCTC CTGGAGGACA GGGACCACCT 3720
CTACAAAAAA TAAAAAAGT ACCTCCCCTG TCTCGCACAG TGTCCCAGGA CCCTGCGGTG 3780
CAGTAGAGGC GCACCAAAAC TTTGTCTCTT GTGATTTCTT TAGCGGCATC AACATACACT 3840
TCTAAGACTC AGCTGATGTG CCCACTGTGG AACAGGCACA CTGCTTGGGG GAGGGAGGAA 3900
```

AAGGAGGGCC ATCAAAATTG CAATAAGCTG GGCCCCTCAC ACACCCAACC CCATCTCAAT    3960

GCTGTCCTGT GAT    3973

( 2 ) INFORMATION FOR SEQ ID NO:7:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:7:

CTTCTTCCTT TCCTTCTCAT CTCAGC    26

( 2 ) INFORMATION FOR SEQ ID NO:8:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:8:

CTCCTGTGCT TCTCGACCAG CATG    24

( 2 ) INFORMATION FOR SEQ ID NO:9:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:9:

GTGGGTGCAG GAGCTCATTC    20

( 2 ) INFORMATION FOR SEQ ID NO:10:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:10:

CAGCGACAGA TCTACATGAG    20

( 2 ) INFORMATION FOR SEQ ID NO:11:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:11:

GACCAGGGAT AAGCAAGATC A    21

( 2 ) INFORMATION FOR SEQ ID NO:12:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:12:

GCGAGAACTC TTCAGGTACT                                                                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

CCCACTAGTT TTCTTAACCC                                                                    20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

ATTCTGCTGG TTGGTGGGGG                                                                    20

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:15:

CTGGGTAGGA TTCGCTTT                                                                      18

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:16:

CAGGTGCTCC TGTGCTTC                                                                      18

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:17:

CTGGGAAAGG AACTGATG                                                                      18

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:18:

TCGGCTGGTA CATCTTCCGC G                                                                  21

( 2 ) INFORMATION FOR SEQ ID NO:19:

( i ) SEQUENCE CHARACTERISTICS:
        ( A ) LENGTH: 110 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
ACACTGAGCA   TGAGAGATGT   GTATCCTTTA   GCCACAGCTC   CAGAGCGAGG   CTAAGGAGCT        60
TGGCTTTGCT   TTCTGTTGTC   GTCTGTTGTG   CCACCCCCAA   AAAAAAAAAA                    110
```

( 2 ) INFORMATION FOR SEQ ID NO:20:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

```
AGTCAGCCAC   TATGAGGAGG   GTCGGGAAGA   ATTTGCGTTT   TCAGTGGAAA   CAAGTGCGTA        60
CTCTATCGAT   GACTGTGATT   GACTCGATCT                                              90
```

( 2 ) INFORMATION FOR SEQ ID NO:21:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
ACATTAAGGA   ATAATTTTTC   CAATTGTTAA   AAACAGTTTG   AAGCGGTTCC   TACTGGGGCT        60
CGTGGGGAAG   GGCTGAAGCG   AATTCCAGCA   CACTGC                                     96
```

( 2 ) INFORMATION FOR SEQ ID NO:22:

( i ) SEQUENCE CHARACTERISTICS:
        ( A ) LENGTH: 136 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

```
TGATCGTCAG   CTGCATGAAT   GACAGACTGT   CATGACTATC   CCTGTCGACT   GCACCAGTCT        60
CGCCCTCTCA   CGTCCTTGGC   GCTATGAGGG   CACATGTTGA   ATCACAGTAA   ATTATTTGAT       120
GGTCAAAAAA   AAAAAA                                                               136
```

( 2 ) INFORMATION FOR SEQ ID NO:23:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:23:

```
TGTACACTTA AGTTTTCTGT ACATAAATAT AATTACAAAG TTATCTTCCT TCTTTGGTTC      60
TTTGGGTTGC TGGTCGGAAA AAAAA                                            85
```